US009327087B2

(12) United States Patent
Pearson et al.

(10) Patent No.: US 9,327,087 B2
(45) Date of Patent: May 3, 2016

(54) DISPENSING DEVICE

(71) Applicant: Glaxo Group Limited, Brentford, Middlesex (GB)

(72) Inventors: Allen John Pearson, Huntingdon (GB); Ian Cude, Ware (GB); Paul Kenneth Rand, Huntingdon (GB)

(73) Assignee: Glaxo Group Limited, Brentford, Middlesex (GB)

( * ) Notice: Subject to any disclaimer, the term of this patent is extended or adjusted under 35 U.S.C. 154(b) by 38 days.

(21) Appl. No.: 13/845,844

(22) Filed: Mar. 18, 2013

(65) Prior Publication Data

US 2013/0213394 A1 Aug. 22, 2013

Related U.S. Application Data

(63) Continuation of application No. 10/598,697, filed as application No. PCT/GB2005/000926 on Mar. 10, 2005, now Pat. No. 8,397,714.

(30) Foreign Application Priority Data

Mar. 10, 2004 (GB) .................................. 0405397.1
Sep. 15, 2004 (GB) .................................. 0420538.1

(51) Int. Cl.
*A61M 15/00* (2006.01)
*A61M 11/04* (2006.01)
(52) U.S. Cl.
CPC .............. *A61M 15/00* (2013.01); *A61M 11/04* (2013.01); *A61M 15/009* (2013.01); *A61M 15/0023* (2014.02); *A61M 15/0025* (2014.02); *A61M 15/0096* (2014.02); *A61M 2205/276* (2013.01); *A61M 2205/6045* (2013.01)

(58) Field of Classification Search
CPC .................... A61M 15/0025; A61M 15/0026; B65D 55/16
USPC ............. 128/200.14–200.23, 203.12–204.14, 128/205.23; 222/153.13, 557–559; 215/306; 604/36–38, 187, 207
See application file for complete search history.

(56) References Cited

U.S. PATENT DOCUMENTS

| 197,890 | A | * | 12/1877 | Perry ............................ 215/238 |
| 384,689 | A | | 6/1888 | Heckert |
| 389,707 | A | * | 9/1888 | Kottgen ........................ 215/238 |
| 834,679 | A | * | 10/1906 | Newton et al. ................ 215/243 |
| 1,814,343 | A | * | 7/1931 | Smith ............................. 70/164 |

(Continued)

FOREIGN PATENT DOCUMENTS

| DE | 29818662 U1 | 4/2000 |
| EP | 0075548 B1 | 7/1986 |

(Continued)

OTHER PUBLICATIONS

Anonymous; "Canister retention feature for inhalation device" Research Disclosure; Kenneth Mason Publications, Westbourne, GB; Feb. 1995; vol. 370, No. 34; XP007120212 ISSN: 0374-4353.

*Primary Examiner* — Valerie L Skorupa
(74) *Attorney, Agent, or Firm* — Robert J. Smith

(57) ABSTRACT

A dust cap for a pMDI having a cap part adapted for a push-fit on the dispensing nozzle of the pMDI and a strap part for connecting the dust cap to the pMDI, wherein the cap part is slidably mounted on the strap part for sliding movement between an extended position and a contracted position.

17 Claims, 34 Drawing Sheets

(56) References Cited

U.S. PATENT DOCUMENTS

| | | | |
|---|---|---|---|
| 2,052,260 A * | 8/1936 | Tomita | 215/200 |
| 2,627,996 A | 2/1953 | Dorner | |
| 3,191,867 A | 6/1965 | Helms | |
| 3,255,928 A | 6/1966 | Foster | |
| 3,404,681 A | 10/1968 | Fowler | |
| 3,429,310 A | 2/1969 | Jaffe et al. | |
| 3,549,055 A | 12/1970 | Gatlano | |
| 3,622,053 A | 11/1971 | Ryden | |
| 3,826,413 A | 7/1974 | Warren | |
| 3,830,224 A | 8/1974 | Vanzetti et al. | |
| 3,904,088 A | 9/1975 | Milbourne | |
| 3,927,806 A | 12/1975 | Meshberg | |
| 3,994,421 A | 11/1976 | Hansen | |
| 4,291,688 A | 9/1981 | Kistler | |
| 4,429,799 A * | 2/1984 | Zaltsman | 215/46 |
| 4,509,515 A | 4/1985 | Altounyan et al. | |
| 4,576,157 A | 3/1986 | Raghuprasad | |
| 4,641,644 A | 2/1987 | Andersson et al. | |
| 4,644,107 A | 2/1987 | Clowes et al. | |
| 4,664,107 A | 5/1987 | Wass | |
| 4,771,769 A | 9/1988 | Hegemann et al. | |
| 4,830,224 A | 5/1989 | Brison | |
| 4,834,083 A | 5/1989 | Byram et al. | |
| 4,860,738 A | 8/1989 | Hegemann et al. | |
| 4,921,142 A | 5/1990 | Graf et al. | |
| 4,940,051 A | 7/1990 | Lankinen | |
| 4,944,429 A | 7/1990 | Bishop et al. | |
| 4,969,578 A | 11/1990 | Gander et al. | |
| 5,007,419 A | 4/1991 | Weinstein et al. | |
| 5,031,610 A | 7/1991 | Armstrong et al. | |
| 5,069,204 A | 12/1991 | Smith et al. | |
| 5,119,806 A | 6/1992 | Palson et al. | |
| 5,203,323 A | 4/1993 | Tritle | |
| 5,243,970 A | 9/1993 | Ambrosio et al. | |
| 5,447,150 A | 9/1995 | Bacon | |
| 5,564,583 A * | 10/1996 | Kelley et al. | 220/23.83 |
| 5,687,710 A | 11/1997 | Ambrosio et al. | |
| 5,740,792 A | 4/1998 | Ashley et al. | |
| 5,826,571 A | 10/1998 | Casper et al. | |
| 5,860,416 A | 1/1999 | Howlett | |
| 5,896,853 A | 4/1999 | Howlett | |
| 5,899,200 A * | 5/1999 | McNary | 128/200.14 |
| 6,003,205 A | 12/1999 | Dehaven | |
| 6,062,214 A | 5/2000 | Howlett | |
| 6,105,826 A | 8/2000 | Oursin et al. | |
| 6,173,868 B1 | 1/2001 | DeJonge | |
| 6,182,665 B1 | 2/2001 | Hill et al. | |
| 6,227,399 B1 * | 5/2001 | Angus et al. | 220/375 |
| 6,240,918 B1 | 6/2001 | Ambrosio et al. | |
| 6,261,274 B1 | 7/2001 | Arghyris et al. | |
| 6,302,101 B1 | 10/2001 | Py | |
| 6,354,290 B1 | 3/2002 | Howlett | |
| 6,364,166 B1 | 4/2002 | Ritsche et al. | |
| 6,382,463 B2 | 5/2002 | Meshberg | |
| 6,446,626 B1 | 9/2002 | Virtanen | |
| 6,460,537 B1 | 10/2002 | Bryant et al. | |
| 6,484,715 B1 | 11/2002 | Ritsche et al. | |
| 6,578,741 B2 | 6/2003 | Ritsche et al. | |
| 6,601,735 B2 | 8/2003 | Milian et al. | |
| 6,637,432 B2 | 10/2003 | Wakefield et al. | |
| 6,644,305 B2 | 11/2003 | MacRae et al. | |
| 6,648,158 B1 * | 11/2003 | Lawrence | 215/306 |
| 6,655,380 B1 | 12/2003 | Andersson et al. | |
| 6,672,304 B1 | 1/2004 | Casper | |
| 6,701,917 B2 | 3/2004 | O'Leary | |
| 6,718,972 B2 | 4/2004 | O'Leary | |
| 6,729,324 B2 | 5/2004 | Casper et al. | |
| 6,752,147 B1 * | 6/2004 | Goldemann et al. | 128/203.15 |
| 6,792,941 B2 | 9/2004 | Andersson | |
| 6,953,039 B2 | 10/2005 | Scarrot et al. | |
| 6,964,381 B2 | 11/2005 | Stradella et al. | |
| 7,047,967 B2 | 5/2006 | Knudsen | |
| D529,605 S | 10/2006 | Huxham | |
| 7,131,441 B1 * | 11/2006 | Keller et al. | 128/203.15 |
| D537,936 S | 3/2007 | Cox | |
| D548,330 S | 8/2007 | Cox | |
| D552,729 S | 10/2007 | Cox | |
| 7,464,708 B2 | 12/2008 | Marx | |
| 8,251,056 B2 | 8/2012 | Pearson et al. | |
| 8,397,714 B2 | 3/2013 | Pearson | |
| 8,443,993 B1 * | 5/2013 | Desselle | 215/306 |
| 2002/0056449 A1 | 5/2002 | Wakefield et al. | |
| 2002/0117513 A1 | 8/2002 | Helmlinger | |
| 2003/0052196 A1 | 3/2003 | Fuchs | |
| 2003/0100867 A1 | 5/2003 | Fuchs | |
| 2004/0069301 A1 | 4/2004 | Bacon | |
| 2004/0089292 A1 * | 5/2004 | Pollet et al. | 128/200.23 |
| 2004/0237961 A1 | 12/2004 | Snow et al. | |
| 2004/0245291 A1 | 12/2004 | Simon et al. | |
| 2004/0256414 A1 | 12/2004 | Graf | |
| 2005/0011515 A1 | 1/2005 | Lee et al. | |
| 2005/0040188 A1 | 2/2005 | Herry et al. | |
| 2005/0098583 A1 | 5/2005 | Mbonyumuhire | |
| 2005/0127107 A1 | 6/2005 | Mbonyumuhire et al. | |
| 2008/0060642 A1 | 3/2008 | Bunce | |

FOREIGN PATENT DOCUMENTS

| | | |
|---|---|---|
| EP | 151225 B1 | 3/1988 |
| EP | 227510 B1 | 9/1989 |
| EP | 0428380 B1 | 10/1993 |
| EP | 428380 B1 | 10/1993 |
| EP | 0414536 B1 | 1/1994 |
| EP | 563131 B1 | 9/1996 |
| EP | 929473 B1 | 4/2000 |
| EP | 1066075 B1 | 5/2005 |
| EP | 1384689 B1 | 6/2005 |
| FR | 2682305 A | 4/1993 |
| GB | 1044627 A | 10/1966 |
| GB | 2263873 A | 8/1993 |
| GB | 2264238 A | 8/1993 |
| GB | 2272162 A | 5/1994 |
| GB | 2364320 A | 1/2002 |
| GB | 2385845 A | 9/2003 |
| GB | 2385846 A | 9/2003 |
| GB | 2398252 A | 8/2004 |
| GB | 2419292 A | 4/2006 |
| WO | 91/06333 A1 | 5/1991 |
| WO | 94/05359 A1 | 3/1994 |
| WO | 95/29723 A1 | 11/1995 |
| WO | 97/06842 A1 | 2/1997 |
| WO | 98/52634 A1 | 11/1998 |
| WO | 98/56444 A1 | 12/1998 |
| WO | 99/04840 A1 | 2/1999 |
| WO | 99/25405 A1 | 5/1999 |
| WO | 99/38555 A1 | 8/1999 |
| WO | 99/49916 A1 | 10/1999 |
| WO | 01/21238 A1 | 3/2001 |
| WO | 01/70314 A1 | 9/2001 |
| WO | 01/76668 A1 | 10/2001 |
| WO | 01/87391 A1 | 11/2001 |
| WO | 02/00279 A1 | 1/2002 |
| WO | 02/30503 A1 | 4/2002 |
| WO | 02/30504 A1 | 4/2002 |
| WO | 02/32784 A1 | 4/2002 |
| WO | 02/49698 A1 | 6/2002 |
| WO | 03/020350 A1 | 3/2003 |
| WO | 03/026803 A1 | 4/2003 |
| WO | 03/026804 A1 | 4/2003 |
| WO | 03/026805 A1 | 4/2003 |
| WO | 03/029105 A1 | 4/2003 |
| WO | 03/043909 A2 | 5/2003 |
| WO | 03/061843 A1 | 7/2003 |
| WO | 03/070599 A1 | 8/2003 |
| WO | 03/077975 A1 | 9/2003 |
| WO | 031074189 A1 | 9/2003 |
| WO | 03/080161 A1 | 10/2003 |
| WO | 03/095006 A2 | 11/2003 |
| WO | 03/095007 A2 | 11/2003 |
| WO | 04/001664 A1 | 12/2003 |
| WO | 2004/009454 A2 | 1/2004 |
| WO | 2004/028608 A1 | 4/2004 |
| WO | 2004/041334 A2 | 5/2004 |
| WO | 2004/041339 A2 | 5/2004 |

(56) References Cited

FOREIGN PATENT DOCUMENTS

| WO | 2004/064906 | A1 | 8/2004 |
| WO | 2004/073776 | A1 | 9/2004 |
| WO | 2004/089782 | A2 | 10/2004 |
| WO | 2004/096329 | A1 | 11/2004 |
| WO | 2005/046774 | A1 | 5/2005 |
| WO | 2005/087299 | A1 | 9/2005 |
| WO | 2005/107838 | A1 | 11/2005 |
| WO | 2005/107955 | A1 | 11/2005 |
| WO | 2005/110520 | A1 | 11/2005 |
| WO | 2006/087385 | A1 | 8/2006 |
| WO | 2006/097756 | A1 | 9/2006 |

* cited by examiner

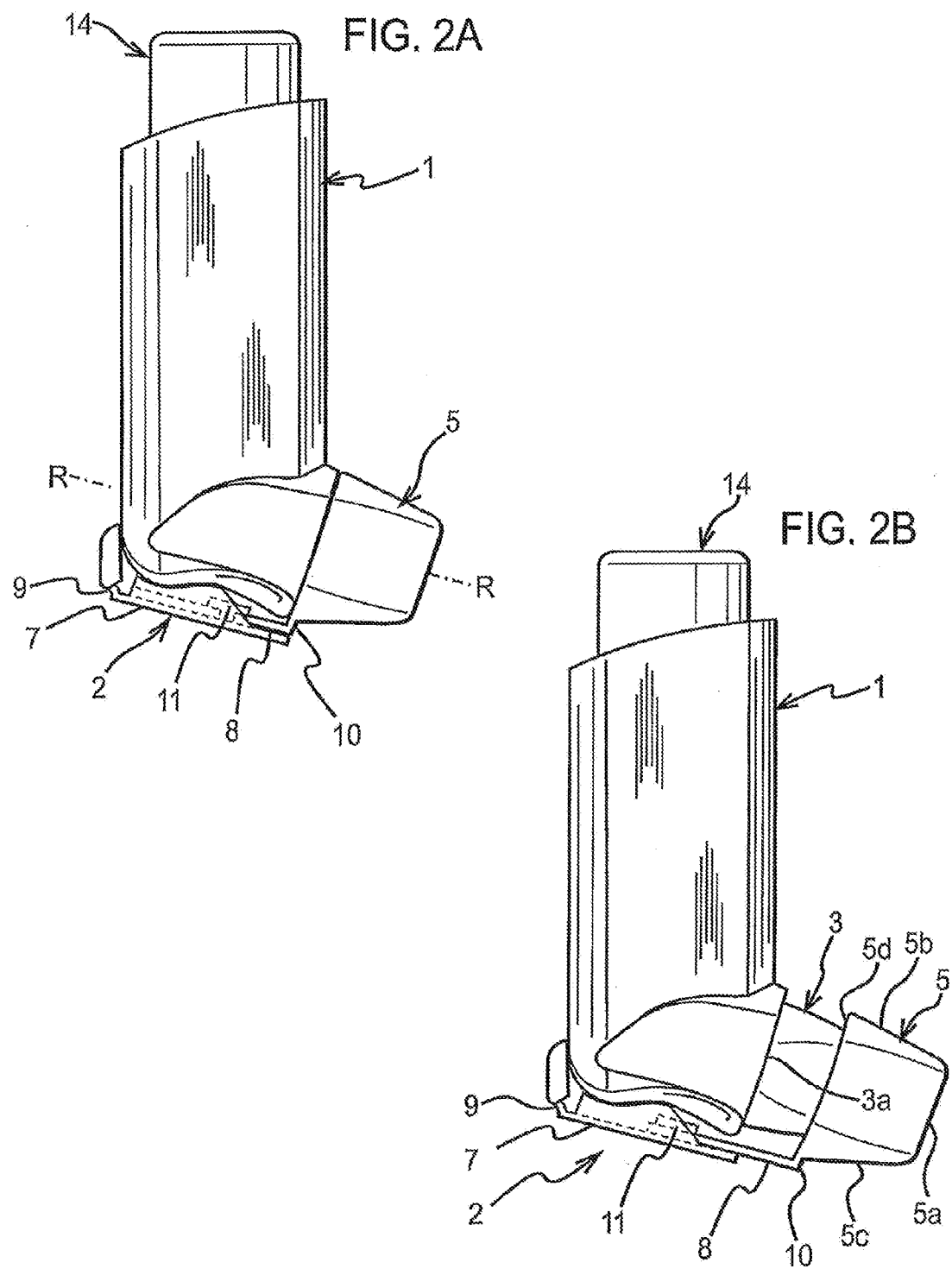

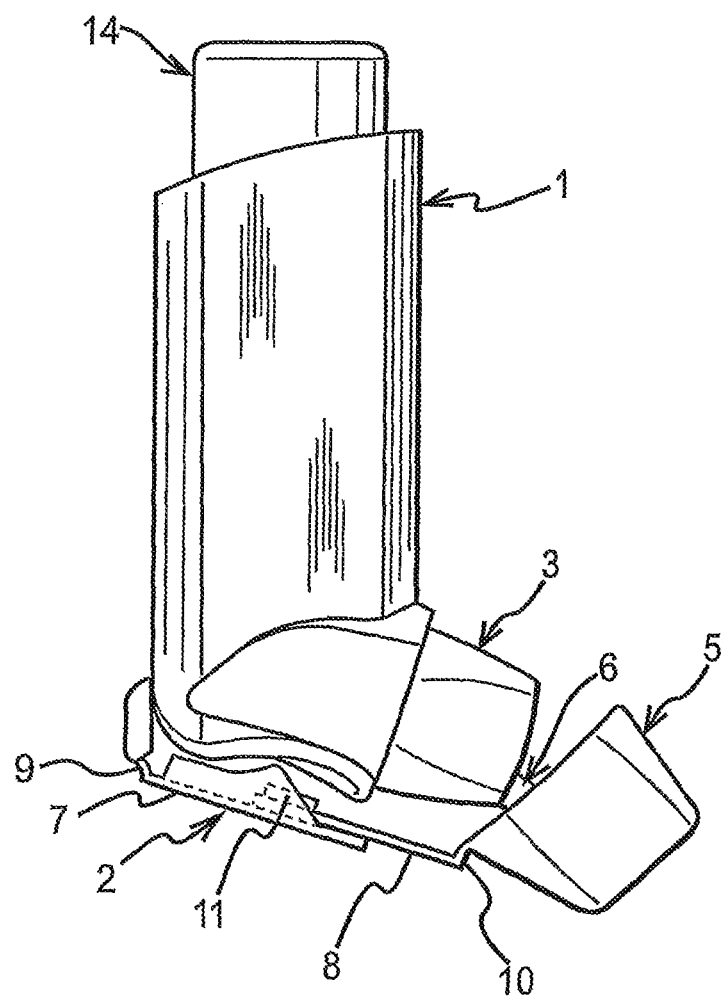

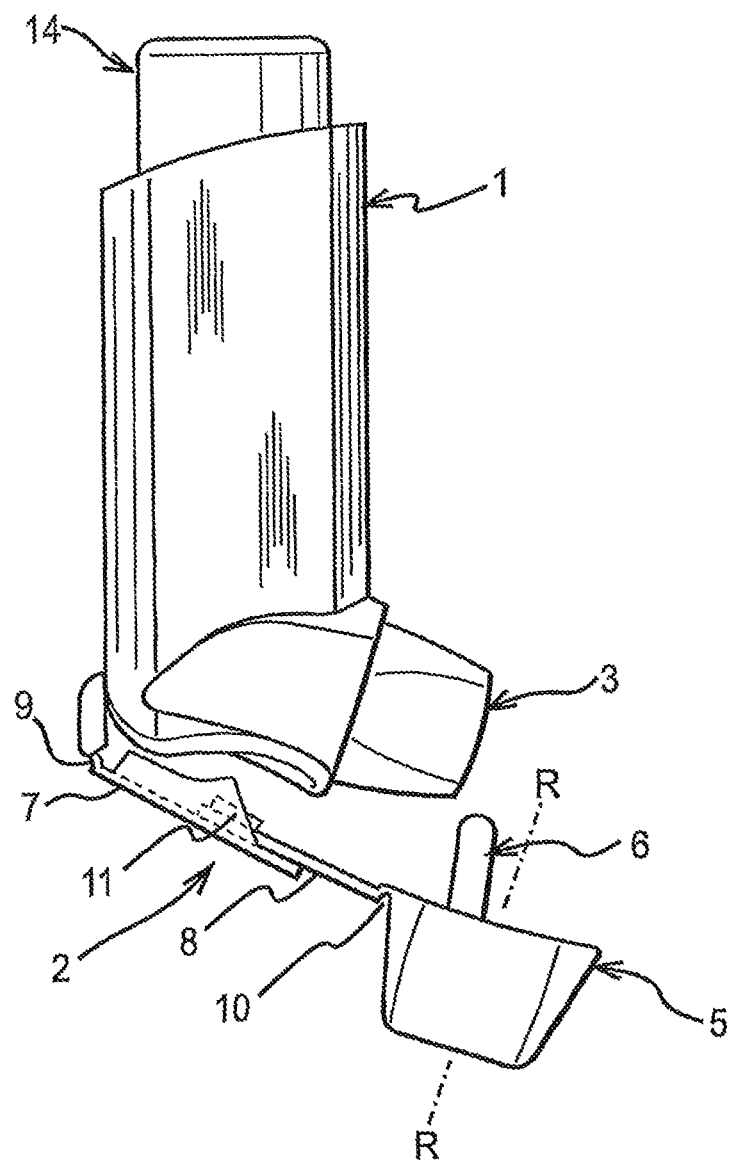

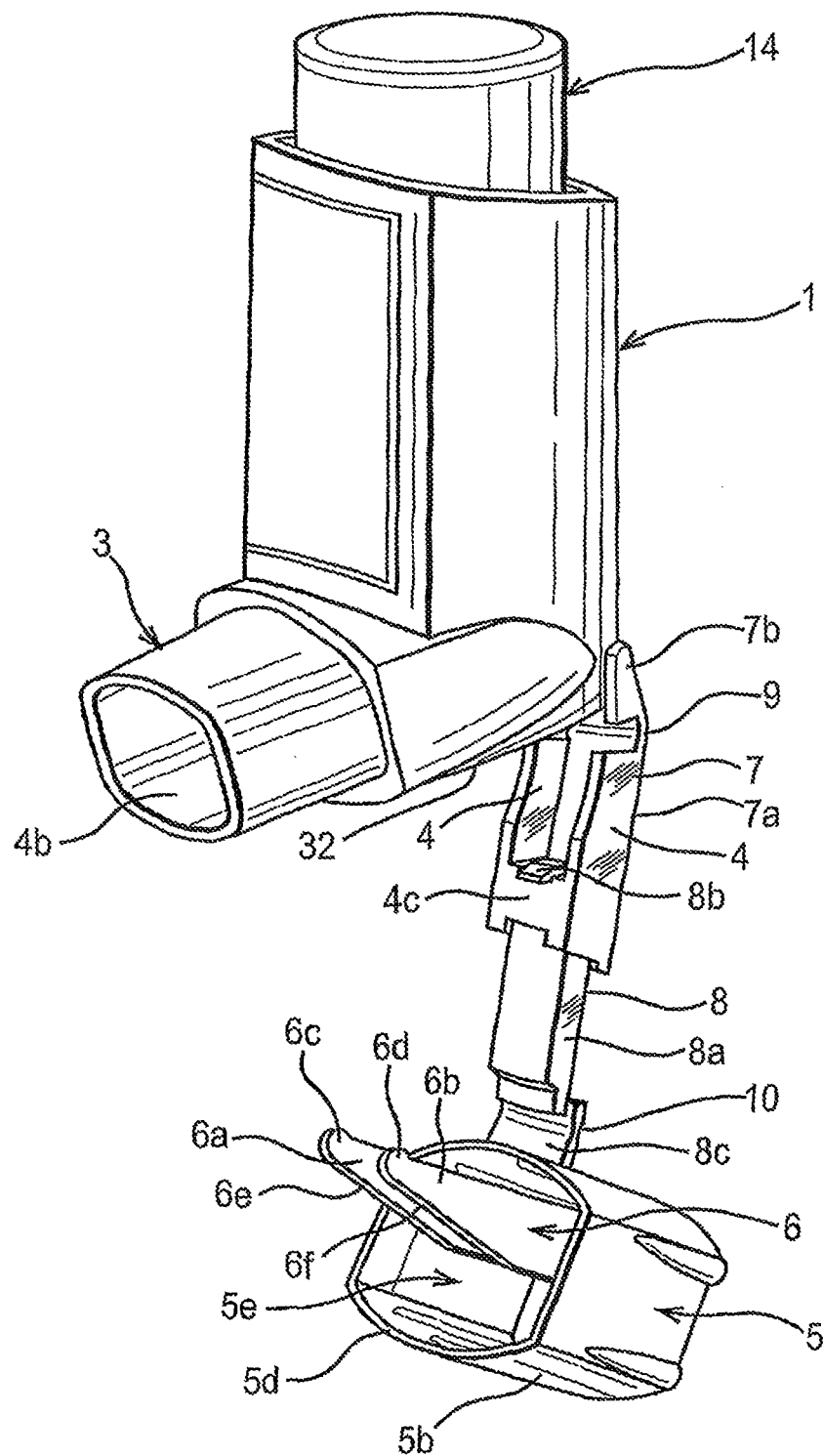

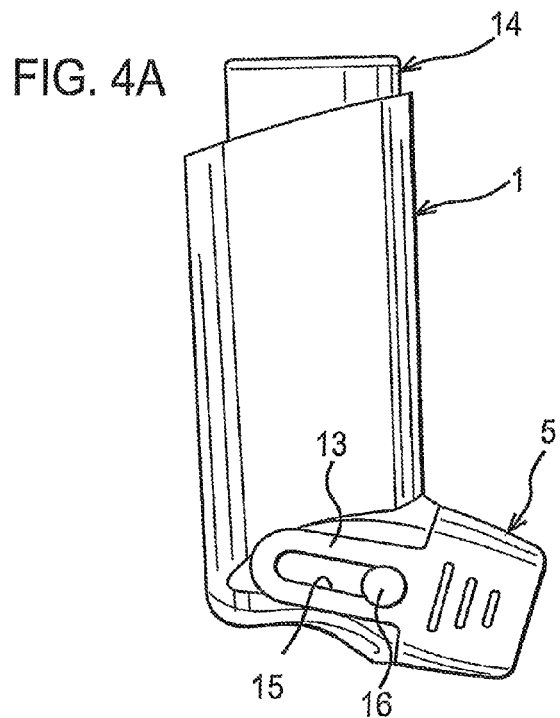
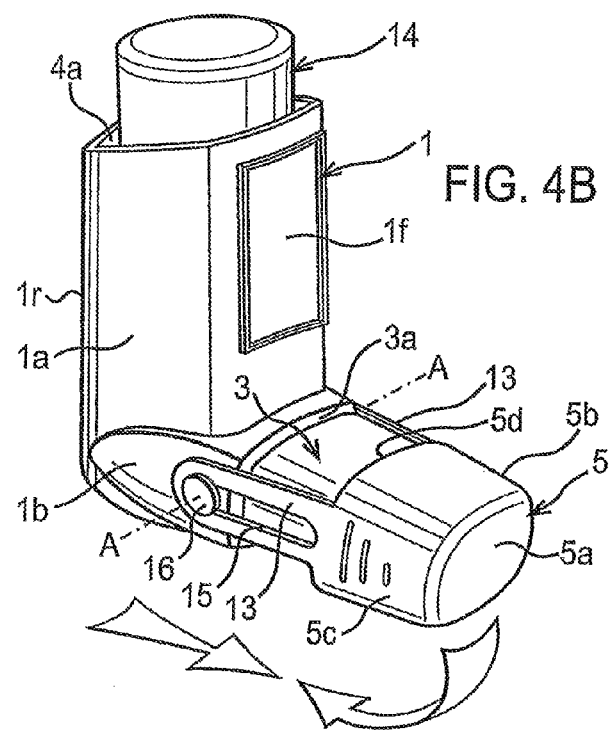

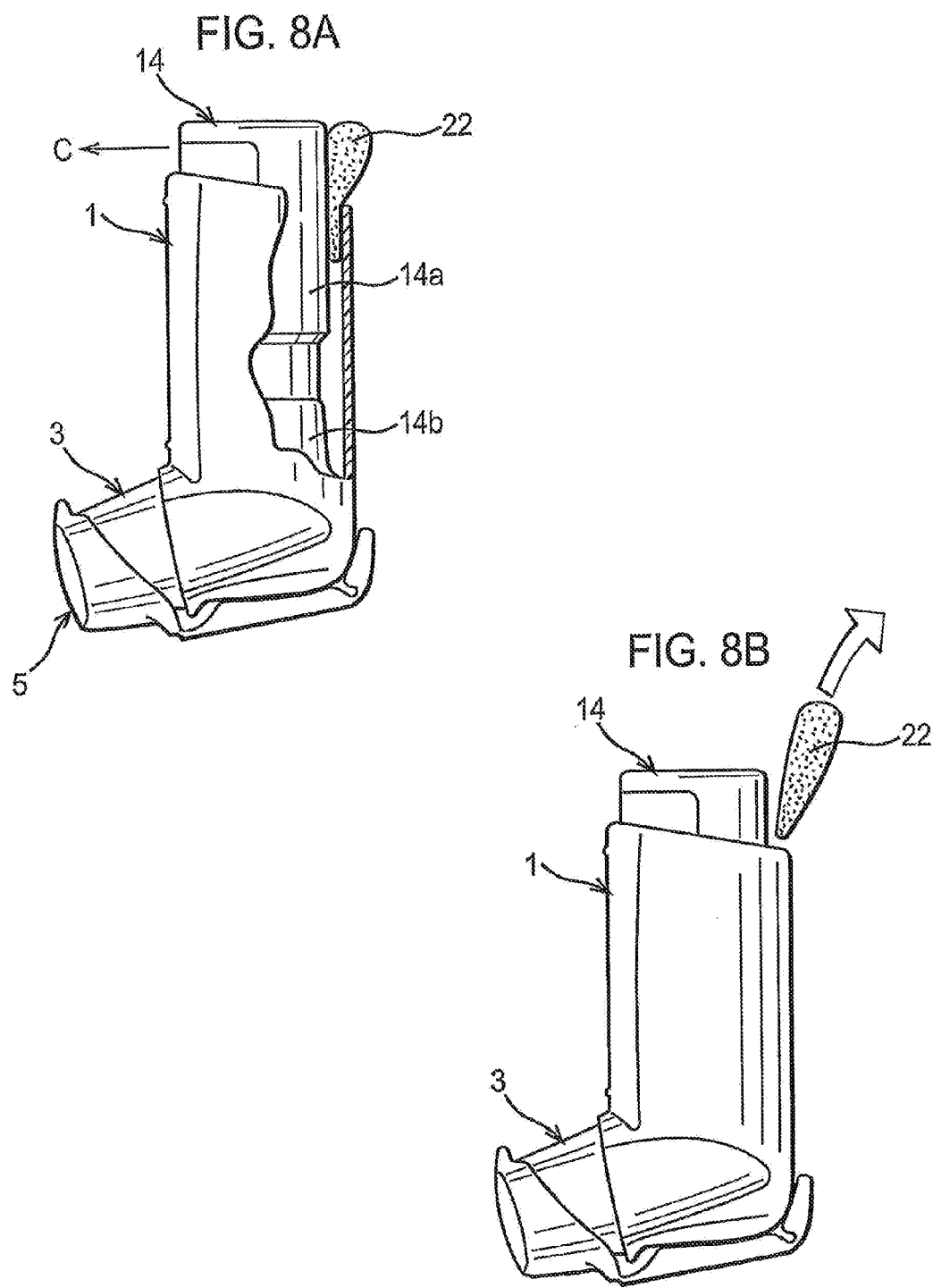

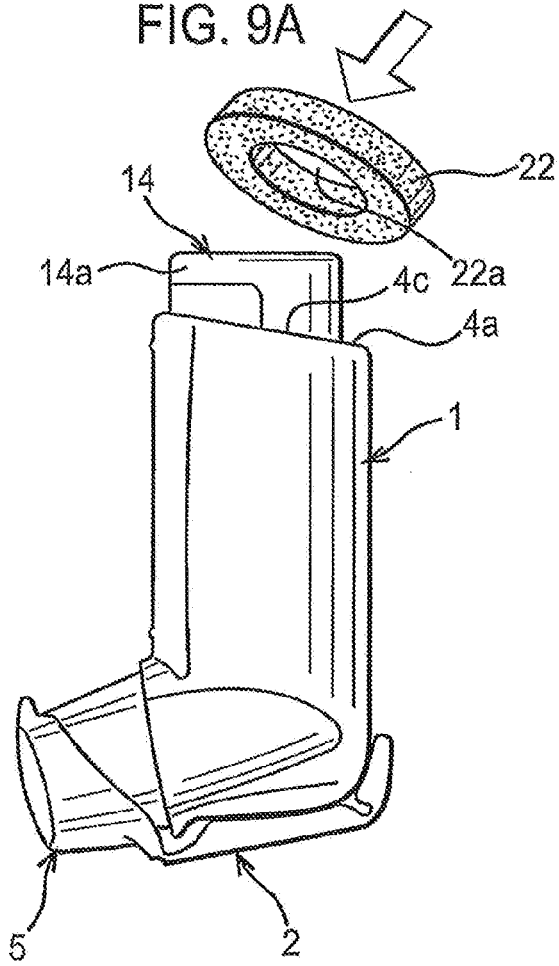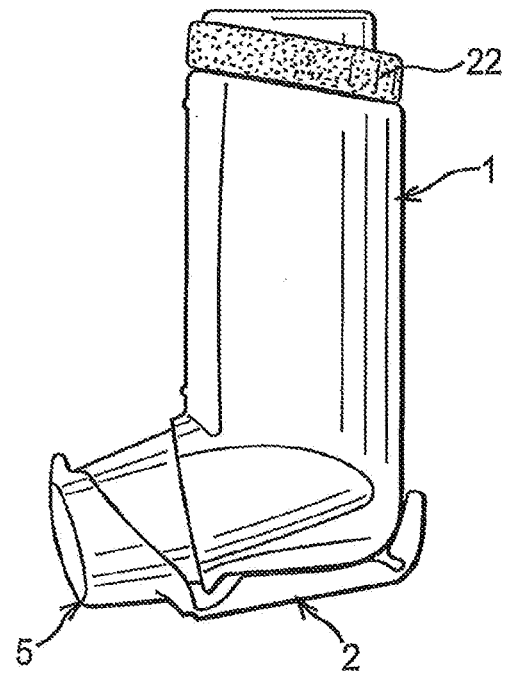

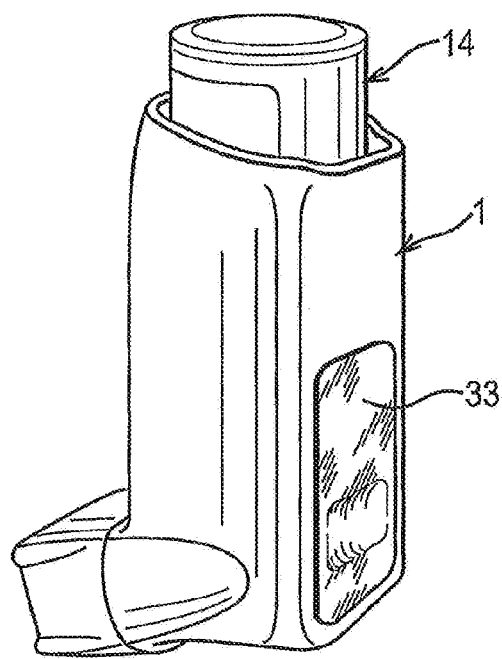
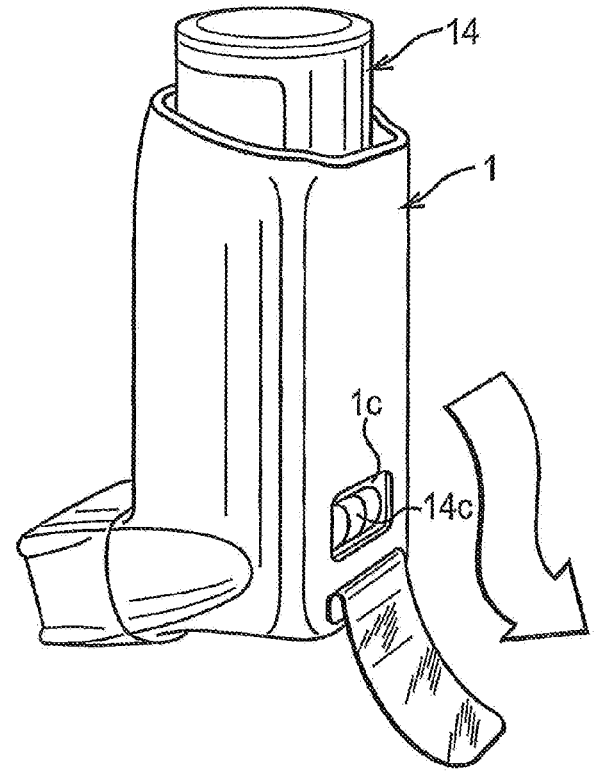

DISPENSING DEVICE

RELATED APPLICATIONS

This application is a continuation of U.S. patent application Ser. No. 10/598,697, filed Sep. 26, 2007, now U.S. Pat. No. 8,397,714, which is a 35 USC 371 US National Phase entry of PCT/GB05/00926, filed Mar. 10, 2005, which claims priority from UK patent application Nos. 0 405 397.1 and 0 420 538.1 respectively filed on 10 Mar. 2004 and 15 Sep. 2004, the entire contents of each of which are incorporated herein by reference.

FIELD OF THE INVENTION

The present invention relates to a dispensing device for dispensing a substance, and is particularly, but not exclusively, concerned with a medicament dispenser from which a medicament formulation is dispensable. The invention also relates to a closure and to an accessory for a dispensing device, for instance a medicament dispenser.

An example of a medicament dispenser to which the invention is particularly, but not exclusively, concerned is an inhaler, for instance a pressurised metered dose inhaler (hereinafter referred to as a "pMDI"). The invention does, however, embrace other inhaler types, for example a dry powder inhaler (DPI), as will be appreciated by the reader skilled in the inhaler art.

BACKGROUND OF THE INVENTION pMDIs are well known in the art of inhalation devices. It is therefore not necessary to describe the construction and operation of a pMDI other than in bare essentials.

A pMDI comprises a canister unit and a housing. The housing is generally tubular, although this is not essential, and generally formed of a plastics material, for instance by moulding. The canister unit comprises an open-ended canister, typically made from a metal such as aluminium. The open end of the canister is sealingly capped by a metering valve assembly. The valve assembly includes a hollow dispensing member or valve stem which projects from the outlet or business end of the canister. The dispensing member is mounted for sliding movement relative to the canister between an extended position, to which the dispensing member is biased by a biasing mechanism in the valve assembly, and a depressed position.

In use, the sealed canister contains a pressurised medicinal aerosol formulation. The formulation comprises the medicament and a fluid propellant, and optionally one or more excipients and/or adjuvants. The medicament is typically in solution or suspension in the formulation. The propellant is typically a CFC-free propellant, suitably a liquid propellant, and may for example be HFA-134a or HFA-227.

Movement of the dispensing member from the extended position to the depressed position results in a metered dose of the aerosol formulation being dispensed from the canister through the dispensing member. Typically, the metering valve assembly is provided with a metering chamber of defined volume. In the extended position of the dispensing member, the content of the canister is placed in fluid communication with the metering chamber through the dispensing member so that the metering chamber is filled with the aerosol formulation. When the dispensing member is depressed, the metering chamber is isolated from the canister inner volume and placed in fluid communication with the external environment through the dispensing member. Thus, the defined volume of the aerosol formulation in the metering chamber is discharged to the external environment via the dispensing member.

Such metering valve assemblies are well known in the art and can be obtained from inter alia Bespak Plc (King's Lynn, Norfolk, United Kingdom) and Valois S.A.S, (Le Neubourg, France).

The housing comprises an internal passageway having an open end. The canister unit is slidable into the internal passageway through the open end with the canister unit being inserted valve assembly first into the internal passageway. A stem block, which receives the dispensing member of the canister when the canister unit is received in the housing in a "rest position", has a passageway with an inlet end for receiving the dispensing member and an outlet end, which faces a dispensing outlet of the housing, typically a mouthpiece or a nasal nozzle. The stem block holds the dispensing member stationary whereby depression of the canister unit from its rest position further into the housing to an "actuated position" causes the dispensing member to be displaced from the extended position to the depressed position relative to the canister. A metered dose of the aerosol formulation will thereby be dispensed out of the dispensing outlet of the housing via the internal passageway of the stem block.

In use, a patient in need of a metered dose of the medicinal aerosol formulation concurrently inhales on the dispensing outlet and depresses the canister unit from the rest position to the actuated position. The inspiratory airflow produced by the patient entrains the metered dose of the medicinal aerosol formulation into the patient's respiratory tract.

Inhalers are commonly provided with a dust cap that covers the dispensing outlet when the inhaler is not in use. The dust cap, when applied, prevents foreign material from entering the housing. This prevents the user from inhaling dust or lint, for example, that might otherwise accumulate in the housing. This is of particular importance where the user suffers from asthma or other respiratory conditions, in which the inhalation of foreign material may cause severe irritation.

Developments to pMDIs have included the provision of actuation indicators or dose counters therefor. Such a dose counter is described in PCT Patent Application Nos, WO-A-9856444 and WO-A-2004/001664 to Glaxo Group Limited. The pMDI canister unit may comprise the dose counter, which is fixably secured on the valve assembly end of the canister and includes a display which denotes the number of metered doses of the medicament formulation dispensed from, or remaining in, the canister. The display of the dose counter is visible to the patient through a window provided in the housing. The display may be presented by a plurality of indicator wheels rotatably mounted on a common axle, each wheel having numerals from '0' to '9' displayed in series around the circumference.

pMDI devices, however, are susceptible to unintentional actuation, particularly whilst in transit, for example shipment between the manufacturer and distributor. During such transit, such devices and their packaging are often subjected to impacts and sudden movements. Such forces can actuate the pMDI, causing doses of the formulation to be dispensed. When the pMDI includes a dose counter, rough handling in transit can cause the value displayed to the user by the counter to increase or decrease so that it is not consistent with the number of doses that have been dispensed by, or remain in, the pMDI. It is wasteful to dispense unwanted doses of the medicament, and potentially very dangerous for a dose counter to indicate to the user that more doses remain in the canister than are actually present.

It is therefore desirable to provide a pMDI that is adapted to prevent unintentional actuation. It is also desirable to provide a pMDI with a dose counter which is adapted to prevent miscounting actuations in the event of an impact.

A multiple-dose DPI with means of preventing unintentional actuation is marketed under the trademark Easyhaler®, the basic inhaler construction being illustrated in WO-A-01/87391 (Orion Corporation). The Easyhaler® inhaler dispenses a powdered medicament when a dosing member is moved, relative to the body of the inhaler, towards a metering drum. This movement causes the drum to rotate, dispensing a single metered dose of the powdered medicament from a powder reservoir at an inhaler mouthpiece for entrainment in the inhalation airflow of a user inhaling thereat, and driving a dose counting mechanism. The inhaler also comprises a small hole through the body of the inhaler, situated above the mouthpiece. A cap is provided, to cover the mouthpiece when not in use, comprising a prong that protrudes through the hole and into the body of the inhaler when the cap is engaged by the mouthpiece. The presence of the prong inside the body of the inhaler restricts the motion of the dosing member in the direction of the drum, preventing the user from dispensing powder by pressing down on the dosing member while the cap is engaged.

There are, however, a number of disadvantages with the Easyhaler® inhaler. Should moisture enter the inhaler, the powder will agglomerate to form lumps that cannot enter the metering drum, thus affecting the dosage. Also, the interior surface of the mouthpiece is likely to become moist during use, causing the powdered medicament to stick to its interior surface.

Both DPIs and pMDIs mix a medicament with an air stream that is drawn through the device by the user's inhalation and the profile of the inhalation airflow within the housing of the inhaler is therefore important to product performance, for instance the fine particle mass (fpm) or respirable fraction of the emitted dose, as will be well understood by the skilled reader in the inhaler art. Providing a hole in the housing, as in the Easyhaler® device, alters the inhalation airflow profile through the device. Therefore, if an existing inhaler design is adapted to include a prong and hole arrangement, it would require re-testing for regulatory approval. This re-testing delays production and involves additional expense.

Consequently, it would be advantageous to provide a means for preventing accidental actuation of the inhaler without altering the inhalation airflow profile through the housing.

Another problem with the prior art Easyhaler® inhaler is that an adapted cap, provided with a prong, can only be used with inhalers that have been specially provided with a hole above the mouthpiece. The effect of this is that the cap is not reverse-compatible with previously manufactured housings and that the manufacture of the housing needs to be updated.

Some prior art inhalers comprise a strap that is used to secure the dust cap to the housing. This is particularly so of inhalers produced for the US market, where dust caps are required to be attached to the housing. Prior art straps commonly comprise an otherwise rigid plastic strip that can be flexed only at fold-lines provided close to points of attachment to the back of the housing and the dust cap, located at opposite ends of the strap. The roof of the dust cap comprises only a narrow lip and the sides cut away accordingly. In applying the dust cap, the user brings the strap along the bottom of the housing, using the flexibility in the fold lines, and forces the lip over the roof of the dispensing outlet to engage it.

There are a number of problems with this strap. The first is that the lip of the dust cap requires the application of some force to engage it with the housing. Consequently, the dust cap may be difficult for people with weak fingers, for example the arthritic, to apply and remove. A second problem is that continual folding weakens the fold lines in the strap, which may break after a large number of folding actions.

An additional problem is present in those inhalers that comprise a prong attached to the dust cap. In order to enter the housing, the prong must be inserted in a particular orientation. The prior art strap and cap arrangements, discussed above, require the cap to be rotated, about a fold line, into position when it is applied. Accordingly, if the cap is to comprise a prong which must engage, for example, a hole in the housing, the sweeping motion of the prong as the cap rotates would present a problem.

It is therefore desirable to provide an inhaler with means of attaching a dust cap to the dispensing outlet that, whilst being secure when attached, is easy to apply and remove and does not limit the use of a prong, or similar restricting means, to prevent inadvertent actuation of the inhaler.

Other aims of the invention will be understood by what now follows.

SUMMARY OF THE INVENTION

One aspect of the present invention provides an inhaler for use with a container unit containing a medicament formulation to be dispensed, comprising a housing in which the container unit is relatively movable thereto to cause dispensing of a dose, preferably a metered dose, of the medicament formulation from the container unit for inhalation by a user through a dispensing outlet of the housing; a closure positionable to close the dispensing outlet; and a restricting member, provided on the closure, movable between a first position which enables relative movement between the container unit and the housing for dispensing of the dose of the medicament formulation, and a second position in which the restricting member restricts relative movement between the container unit and the housing such that dispensing of the dose of the medicament formulation is prevented; wherein when the closure is positioned to close the dispensing outlet, the restricting member enters the housing through the dispensing outlet to be disposed in its second position.

This aspect of the invention, and others herein disclosed, is particularly advantageous since a prior art housing may be used. This reverse-compatibility is advantageous for the user, who can fit a closure (e.g. a dust cap) with a restricting member to an existing inhaler that he already owns, to the manufacturer, who is not required to change his manufacturing process for the housing, and also for the marketer, who will not need to seek new regulatory approval for an adapted housing.

In an embodiment of the invention, such as one hereinafter to be described, the container unit is a pressurised canister unit, optionally including a dose counter, for instance mounted at the leading end of the canister unit.

In an embodiment of the invention, such as one hereinafter to be described, the restricting member is configured as a clip that engages a surface of the housing and/or container unit, suitably the stem block and/or a step in the housing. This is advantageous since it secures the closure to the housing whilst the inhaler is not in use. Moreover, it secures the restricting member in its second position. In an embodiment of the invention, such as one hereinafter to be described, the clip configuration of the restricting member is such that, if the container unit is moved in its dispensing direction relative to the housing, it causes the gripping force of the restricting member to increase ensuring that the closure is not ejected and dispensing does not occur.

In another aspect of the invention there is provided an inhaler comprising a housing having a dispensing outlet and a closure for closing the dispensing outlet which comprises an extendible connector part for connecting the closure to the housing.

Attaching the closure to the housing is a regulatory requirement in the United States and is in any case beneficial since it prevents loss of the closure or swallowing of it by the user. A particular advantage of an extensible connector (e.g. a strap) is that it reduces the force required to engage and disengage the closure. This is particularly important since many users of inhalers are elderly or infirm and may have weak fingers.

Optionally, the closure may comprise a restricting member. The presence of a restricting member is in itself desirable, as discussed above, and the connector comprised by the present invention is particularly suited to use with closures that comprise a restricting member and that must therefore be spaced sufficiently in front of the housing dispensing outlet that the restricting member can be correctly orientated before the cap is engaged.

In another possible embodiment, the restricting member is attached to the connector.

In an embodiment of the invention, such as one hereinafter to be described, the connector is telescopic and may comprise a first component attached to the housing and a second component attached to the closure, wherein the components are slidingly movable relative to each other between a contracted position, wherein the closure closes the dispensing outlet, and an extended position, wherein the closure is spaced from the dispensing outlet. The two components may be connected using a pin on one component that is held captive within a slot in the other component. At least one of the components may comprise hinging means, for example a fold line. Additionally, raised edges may be provided on one of the components, to substantially prevent relative rotational movement of the components.

In another possible embodiment, the connector may be a strap, and this strap may be made of a flexible and elastically stretchable material, for example knitted elastic, and is stretchable between a contracted state, wherein the closure can be engaged by the dispensing outlet, and an extended state, wherein the closure can be disengaged from the dispensing outlet.

In another possible embodiment, the connector comprises a sliding hinge joining the closure to the housing such that the closure and the housing are capable of relative movement between a first position, wherein the closure closes the dispensing outlet, and a second position, wherein the closure is spaced from the dispensing outlet such that access to the dispensing outlet is substantially unobstructed by the dust cap. This sliding hinge may, in a possible further embodiment, comprise first and second pins located on opposing sides of the dispensing end and first and second slots located on first and second opposing elongated sides of the closure, wherein the pins are captive within in the slots but capable of rotational and sliding movement within them.

In further possible embodiments, the inhaler may be a pMDI and the medicinal formulation may be a medicinal aerosol formulation.

Other aspects and features of the present invention are set forth in inter Ala the claims appended hereto.

Each aspect of the invention may incorporate one or more of the other aspects of the invention or one or more features from the other aspects of the invention.

Further aspects and features of the invention are set forth in the non-limiting exemplary embodiments of the invention which will now be described with reference to the accompanying Figures of drawings.

BRIEF DESCRIPTION OF THE DRAWINGS

FIGS. 2A-2D illustrate the action of disengaging the dust cap of the embodiment shown in FIG. 1.

FIGS. 3A-3J are various views of a pMDI according to another embodiment of the present invention.

FIGS. 4A and 4B show another embodiment of the present invention, wherein a dust cap is provided with elongated sides and is attached to a pMDI by slidable hinges.

FIGS. 8A and 8B show a yet further embodiment of the present invention wherein a restricting member is inserted between a canister unit and the inner surface of the housing of a pMDI, substantially preventing relative movement therebetween.

FIGS. 9A and 9B show a further embodiment of the invention in which a restricting member is mounted on the trailing end of the canister unit of a pMDI.

FIGS. 11A and 11B show yet another embodiment of the invention in which a restricting member is adhesively secured to the canister unit and the housing of a pMDI.

DETAILED DESCRIPTION OF THE EXEMPLARY EMBODIMENTS

Figure 1:
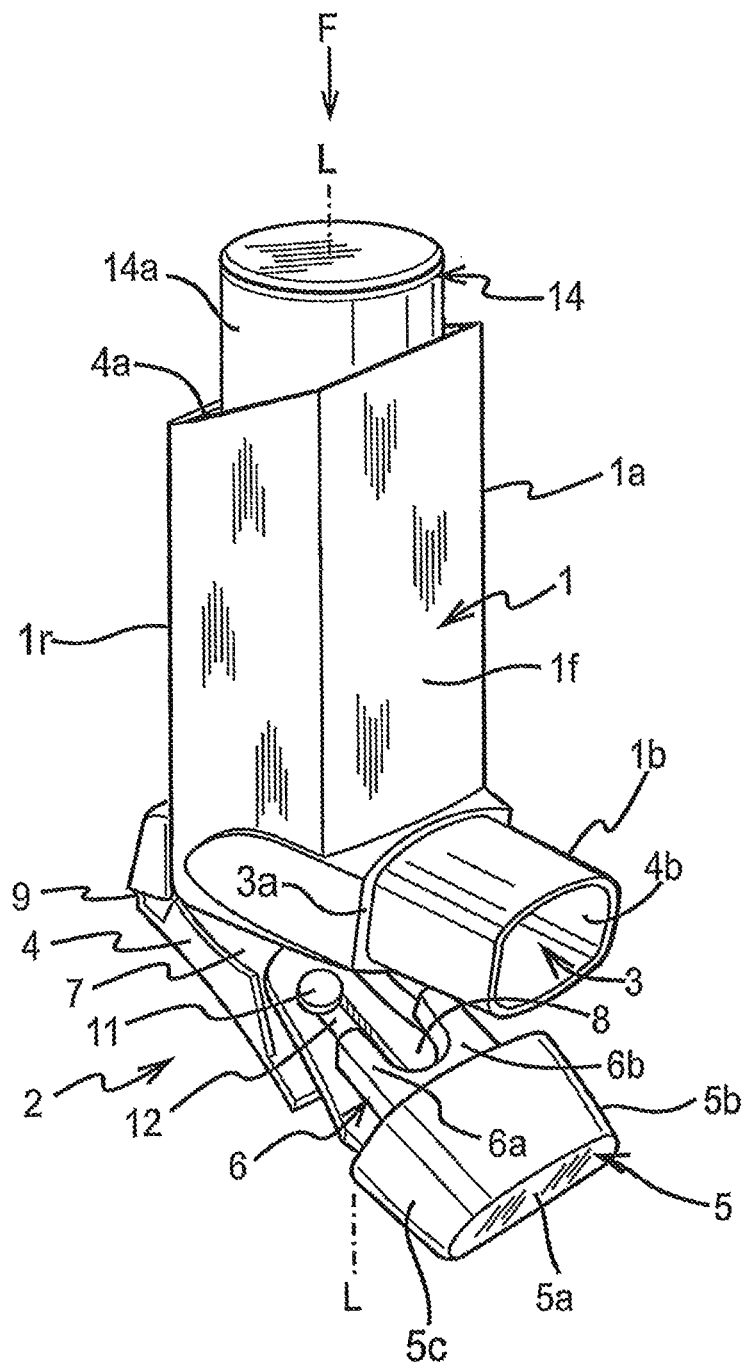
FIG. 1 shows a pMDI, having a dust cap comprising a restricting member, that is provided with a telescopic strap according to an embodiment of the present invention.

In the following description like reference numerals have been used to indicate like parts in the different embodiments of the invention. Each embodiment is comprised in a pMDI which is hand-held and hand-operable.

FIGS. 1 and 2 are respectively front, perspective and side views showing a pMDI according to a first embodiment of the present invention. In this embodiment, the pMDI is based on a pMDI known in the prior art, as described in the 'Background of the Invention' section supra, although the present invention is not limited to the exact form of such an arrangement.

The pMDI comprises a canister unit 14 and a housing 1 in which the canister unit 14 is slidable along its longitudinal axis L-L. The housing 1 is generally tubular and of L-shape having an axial section 1a and a transverse section 1b configured as a mouthpiece 3. The housing 1 is preferably moulded from a plastics material, for example by injection moulding. Conveniently, the housing is of polypropylene. In the use orientation of the pMDT shown in FIGS. 1 and 2, the housing 1 has an upper open end 4a in the axial section 1a, through which the canister unit 14 is reversibly slidable into the housing 1, and a lower open end 4b in the mouthpiece 3.

The canister unit 14 comprises a pressurised canister 14a having a metering valve (see reference numeral 50, FIG. 6F) at its leading or business end and a dose counter module (see reference numeral 14b, FIG. 6) mounted on the leading (valve) end of the canister 14a. The dose counter module 14b is as described and shown in WO-A-2004/001664 supra, the content of which is incorporated herein by reference in its entirety. The canister 14a contains a pressurised medicinal aerosol formulation, as known in the art and mentioned briefly hereinabove.

In use, a patient in need of a metered dose of the medicinal aerosol formulation places his or her lips on the mouthpiece 3 of the housing 1 and then concurrently inhales and, with their finger(s), depresses the canister unit 14 into the housing 1 (arrow F, FIG. 1) to cause the metering valve 50 to release a metered dose of the medicinal formulation from the canister unit 14 for entrainment in the inspiratory airflow produced by the patient for deposition in their lungs. The depression of the canister unit 14 into the housing 1 also results in the dose counter module 14b recording the release of the dose and showing the number of metered doses left in the canister 14a.

A dust cap 5 is attached to the housing 1 by a telescopic strap 2 comprising first 7 and second 8 components. The first component 7 is attached at one end to the housing 1 by a hinge 9 and has a pin 11 at the opposite end to the housing 1. One end of the second component 8 is attached to the dust cap 5 by a second hinge 10. The second component 8 comprises a linear slot 12, in which the pin 11 of the first component 7 is held captive. As shown in FIGS. 2A-2D, although captive within the slot 12, the pin 11 is free to move along its length and thus the two components 7, 8 are capable of relative sliding motion along the length of the slot 12 between a contracted position, with a maximum overlap of the components 7, 8, and an extended position, with a minimum overlap of the components 7, 8.

As illustrated in FIGS. 2A-D, to remove the dust cap 5, the user pulls it away from the mouthpiece 3 with sufficient force to overcome a snap-fit connection therebetween (not shown), thereby extending the telescopic strap 2 to its extended position. Then, the telescopic strap 2 is pivoted at hinges 9, 10, swinging the dust cap 5 clear of the mouthpiece 3 so that it does not obstruct the mouthpiece 3 so that the pMDI is able to be actuated as described above.

To reapply the dust cap 5, the user moves the telescopic strap 2 about the hinges 9, 10 so that the dust cap 5 is repositioned in front of the mouthpiece 3 and is then pushed towards it, compressing the telescopic strap 2 towards its contracted position. The snap-fit connection reconnects.

Side walls 4 may be provided to substantially prevent relative rotational movement of the components 7, 8 about the pin 11.

From an inside surface of the dust cap 5 there projects a restricting member 6 for restricting movement of the canister unit 14 in the housing 1 when the cap 5 is mounted on the mouthpiece 3 such that inadvertent firing and counting cannot take place.

Figure 3A:
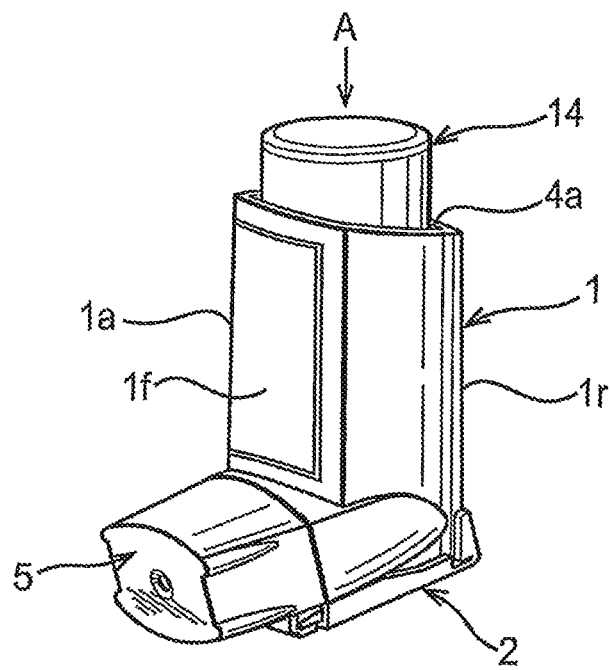
Figure 3B:
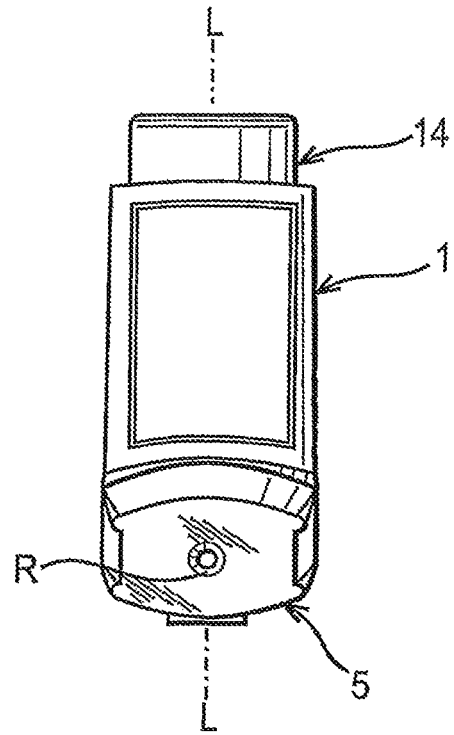
Figure 3C:
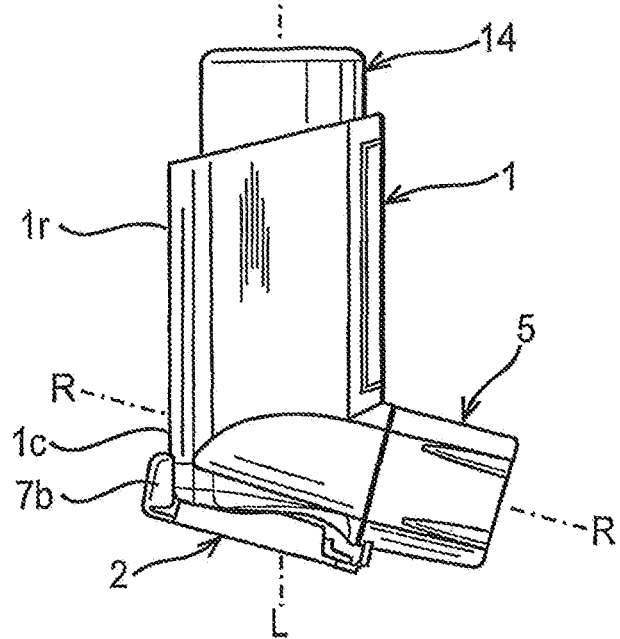
Figure 3D:
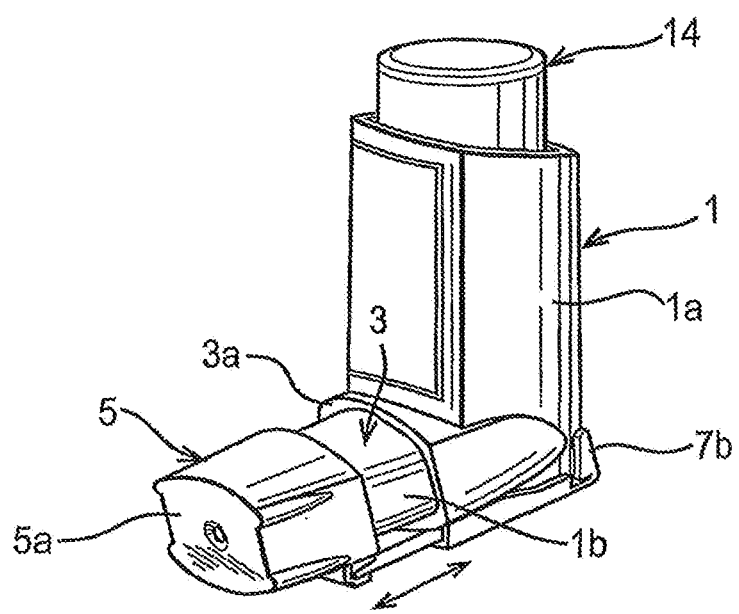
Figure 3F:
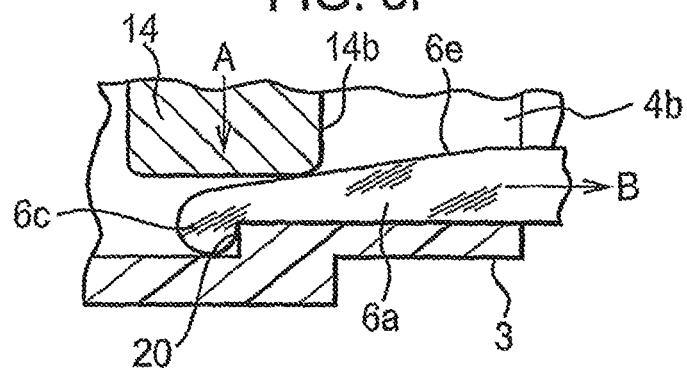

Referring to FIG. 1, the restricting member 6 is in the form of an arm or prong structure comprising a pair of spaced apart arms 6a, 6b. When the dust cap 5 is positioned on the mouthpiece 3, as shown in FIG. 2A, the arms 6a, 6b extend into the housing 1 through the lower open end 4b to straddle the stem block (see reference numeral 18, FIG. 6) for the valve stem to sit underneath the dose counter module 14b at the leading end of the canister unit 14 (as shown in FIGS. 3F and 6F). The arms 6a, 6b prevent the canister unit 14 being depressed sufficiently in the housing 1 to either (a) cause the dose counter module 14b to record a dose release event, or (b) cause the metering valve 50 to open for release of a metered dose of the medicament formulation. The arms 6a, 6b thus prevent inadvertent counting and firing when the dust cap 5 is mounted on the mouthpiece 3, which is nearly all the time as the dust cap 5 is only removed from the mouthpiece 3 when the patient needs a dose of the medicament formulation.

Such inadvertent counting and firing might occur, for example, if the arms 6a, 6b were not present, during shipping of the pMDI from the manufacturer to the distributor, or when the pMDI is in a patient's pocket or handbag, or even as a result of a person fiddling/playing with the pMDI. Wastage of the medicinal formulation is therefore reduced.

Moreover, as a safeguard, the dose counter module 14b is adapted to record release of a metered dose from the canister 14a after depression of the canister unit 14 into the housing by a distance which is less than that required for opening, of the metering valve 50. In other words, the dose counter module is set-up for a 'count-not-fire' event, rather than a 'fire-not- 'count' event, if the pMDI is not used properly. This is because it is preferable for the dose counter display to show that there are less doses left than are actually available than vice-versa. However, it is not easy to depress the canister unit 14 only far enough to cause a 'count-not-fire' event.

In any event, the arms 6a, 6b prevent 'count-not-fire' events occurring while the dust cap 5 is on.

By having the restricting member 6 extend through the mouthpiece 3, no changes need to be made to the housing 1 to accommodate it. Thus, the dust cap 5 can be used with existing pMDI housings. Moreover, the profile of the inhalation airflow through the housing 1, which flows into the housing 1 through the upper open end 4a and out of the housing 1 through the lower open end 4b, is unaffected by the provision of the restricting member 6, since it requires no change to the housing and is removed from the housing prior to use of the pMDI. Consequently, the pharmaceutical performance of the pMDI is unaffected by the provision of the restricting member 6 avoiding the need to obtain new regulatory approval for an existing pMDI product using the new dust cap 5.

It will be appreciated that providing the cap 5 with the telescopic strap 2 provides the cap 5 with the ability to be manoeuvred onto and off the mouthpiece 3 despite it carrying the restricting member 6.

In this embodiment, and the others hereinafter to be described with reference to the FIGURES of drawings, the dust cap 5 and the strap 2 are moulded from polypropylene (PP), although, of course, other materials, in particular plastics materials, and forming techniques, may be used. When the strap 2 is moulded, the hinges 9, 10 are so-called "living hinges". Moreover, the cap 5 is integrally formed with the restricting member 6 and the second component 8 of the strap. The first strap component 7 may be formed separately and then assembled to the second strap component 8. Alternatively, the strap 2 may be integrally formed with the first strap component 7.

FIGS. 3A-3J show a pMDI in accordance with a second embodiment of the invention which corresponds to the first embodiment supra in all respects bar some of the structure of the dust cap 5.

The dust cap 5 has a restricting member 6 in the form of an arm structure comprising a pair of arm members 6a, 6b. The free ends of each arm member 6a, 6b are configured as clips 6c, 6d which, when the cap 5 is mounted on the mouthpiece 3, clip to a step 20 (see also FIG. 6) in the base surface of the housing 1 which supports the stem block (reference 18, FIG. 6). The dips 6c, 6d are formed by providing the free ends of the arm members 6a, 6b as a lollipop profile.

If the canister unit 14 is depressed into the housing 1 while the cap 5 is mounted on the mouthpiece 3, the leading end of the canister unit 14 will push down on the upper surfaces 6e, 6f of the arms 6a, 6b which, as shown schematically in FIG. 3F, have a tapered or ramp profile. More particularly, when the cap 5 is located on the mouthpiece 3, as in FIG. 3F, the upper surfaces 6e, 6f of the cap arms 6a, 6b taper upwardly in the outward or dispensing direction (arrow B). Thus, when the canister unit 14 is depressed into the housing 1 along its axis L-L (arrow A), its leading end abuts the upper surfaces 6e, 6f of the cap arms 6a, 6b tending to push the cap 5 outwardly (arrow B). However, this results in the clips 6c, 6d engaging the step 20 more firmly preventing ejection of the cap 5 and thus inadvertent counting and firing.

In the second embodiment the first component 7 of the telescopic strap 2 has a distal track member 7a with opposed side walls 4. At the distal end of the track member 7a the side walls 4 are bridged by a bridging element 4c. At the proximal end of the first component 7 there is a hinge member 7b which is secured to the housing 1. The track and hinge members 7a, 7b are hinged together by the hinge 9 whereby the track member 7a is hingable about the hinge member 7b.

As regards the second component 8 of the telescopic strap 2, this has a proximal slide member 8a which is linearly slidable in the track member 7a and guided in its linear stroke by the side walls 4. The slide member 8a has a resilient finger 8m at its proximal end which presents a stop element 8b which engages with the bridging element 4c to demark the extended position of the strap 2 and to keep the slide member 8a captive in the track member 7a. At the distal end of the second component 8 there is provided a hinge member 8c hinged to the slide member 8a through the hinge 10. The hinge member 8c of the second component 8 is carried by the dust cap 5.

Figure 3G:
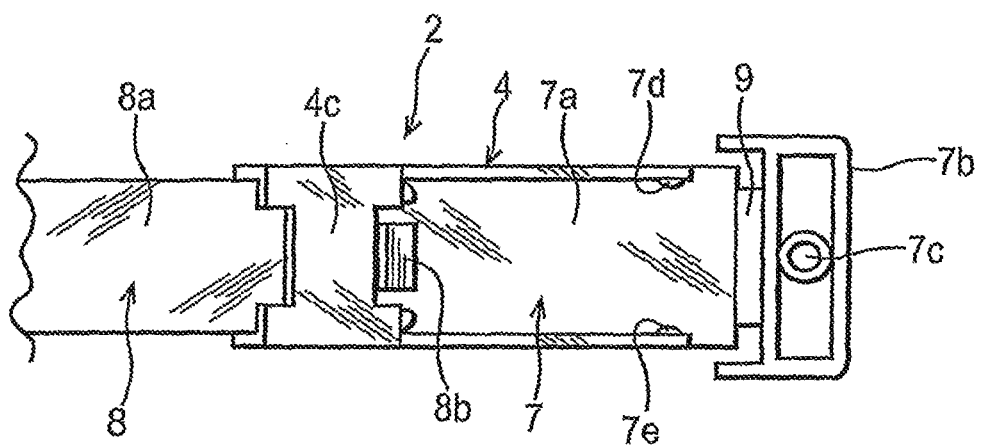
Figure 3H:
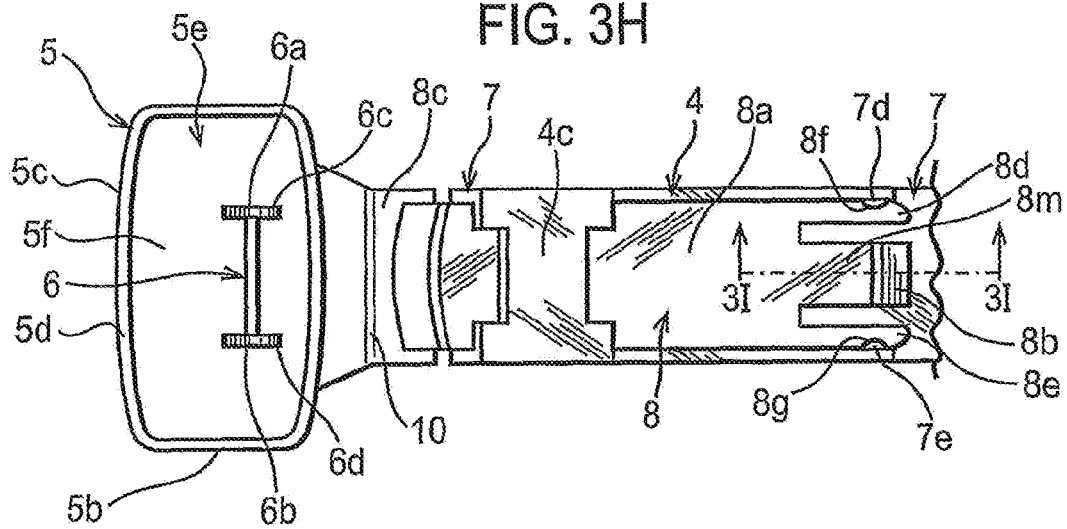

FIGS. 3G and 3H are schematic, fragmentary plan views of the telescopic strap 2 showing in greater detail the strap 2 in its extended and contracted configurations, respectively.

Figure 3I:
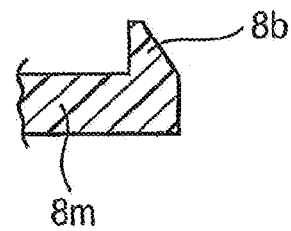
Figure 3J:
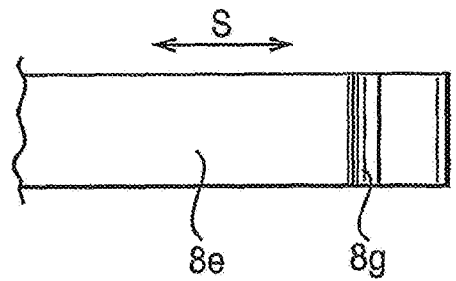

In FIG. 3G there is shown the engagement of the stop element 8b with the bridging element 4c to demark the extended position. FIG. 3I is a cross-sectional view of the stop element 8b taken on line 3I-3I in FIG. 3H. The stop element 8b has a saw-tooth profile and this enables the slide member 8a to be assembled to the track member 7a by sliding of the proximal end of the slide member 8a under the bridging element 4c at the distal end of the track member 7a. The resilience of the finger 8m enables the stop member 8b to go under the bridging element 4c when pushed towards the hinge member 7b until it clears the bridging element 4c whereupon the finger 8m biases the stop element 8b upwardly so that it will abut the bridge element 4c when the slide member 8a is moved in the opposite direction.

FIG. 3G also shows that the hinge member 7b has an aperture 7c therethrough for receiving therein a stud (not shown) on the rear it side of the housing 1 to connect the hinge part 7b to the housing 1, as shown in FIGS. 3A-3E.

From FIG. 3H it will be seen that the proximal end of the slide member 8a is configured as a trident with the stop element 8b being on the middle finger 8m thereof. The outer fingers 8d, 8e of the trident are resilient fingers and on their outer surface which faces the opposing side wall 4 there is provided an elongate slot 8f, 8g, a schematic side view of which is shown in FIG. 33 with arrow 8 indicating the sliding direction of the slide member 8a on the track member 7a.

As shown in FIGS. 3G and 3H, the outer surfaces of the side walls 4 facing the slide member 8a are each provided with an elongate rib 7d, 7e of complementary shape and dimension to the slots 8f, 8g in the outer fingers 8d, 8e of the trident. When the slide member 8a slides on the track member 7a to the contracted position shown in FIG. 3H, for instance when the dust cap 5 is push-fit back onto the mouthpiece 3, the slots 8f, 8g on the outer fingers 8d, 8e snap-fit with the ribs 7d, 7e to securably, releasably fasten the strap 2 in the contracted position. This fastening mechanism may be the sole fastening mechanism (other than the clips 6c, 6d) for securing the dust cap 5 on the mouthpiece 3. There may also be a releasable fastening connection between the dust cap 5 and the mouthpiece 3 (e.g. features 19a and 19b in FIG. 6F).

Figure 3K:
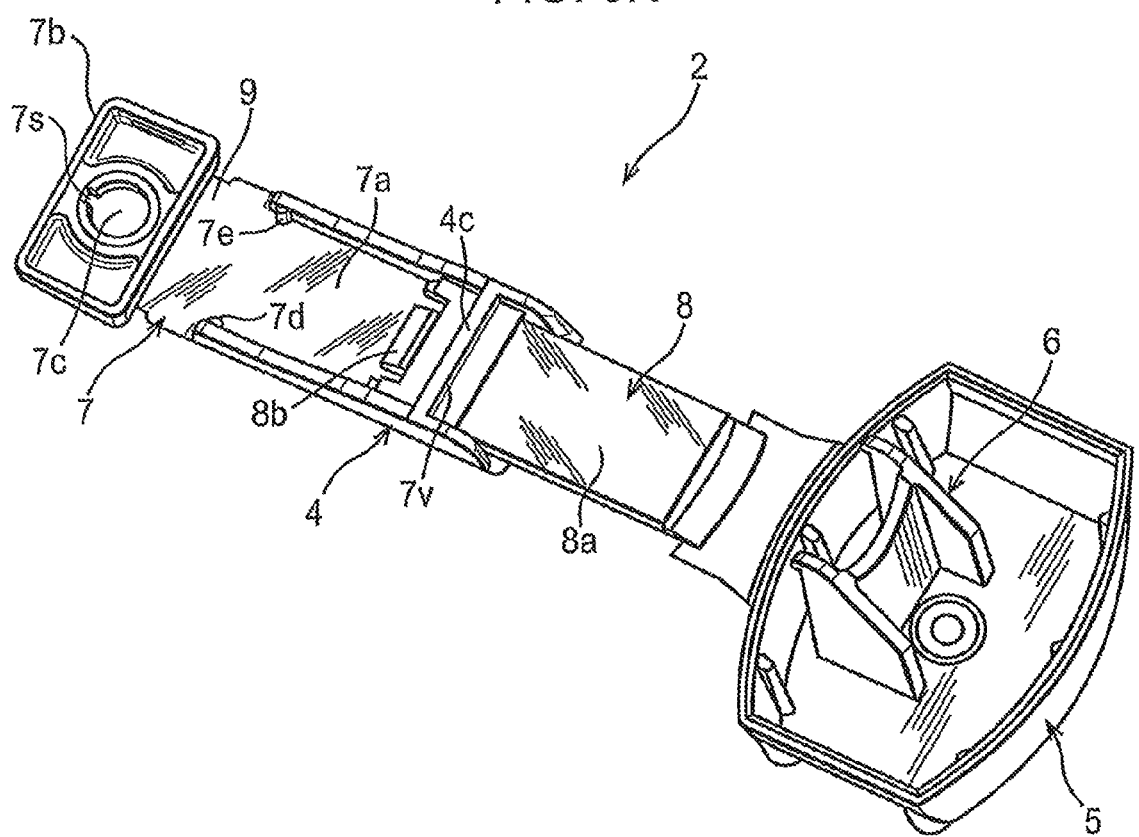
FIGS. 3K-3M are various views of a modification of the embodiment illustrated in FIGS. 3A-3J.
Figure 3L:
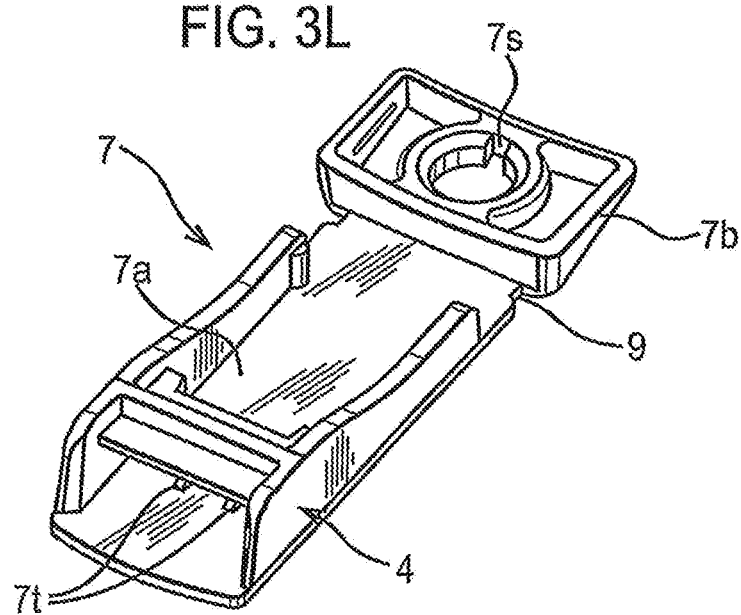
Figure 3M:
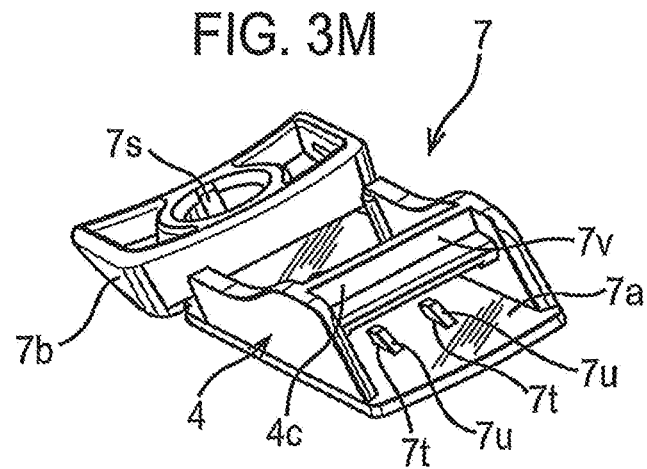

FIGS. 3K-3M show the dust cap 5 and telescopic strap 2 arrangement of FIGS. 3A-3J, but with the first component 7 of the strap 2 incorporating some modifications thereto.

Firstly, the aperture 7c in the hinge member 7b is provided with a slot 7s in its boundary wall. The slot 7s provides the aperture 7c with greater flexibility when receiving the stud (not shown) for assembly of the strap 2 to the housing 1. The aperture 7c is therefore unlikely to split.

Secondly, as shown particularly in FIG. 3M, the track member 7a is provided with raised features 7t underneath the bridging element 4c. These are added to minimise the flexibility of the slide member 8a of the second component 8 of the strap 2 so as to make it harder for the first and second components 7, 8 of the strap 2 to be disassembled. That is to say, the raised features 7t increase the force needed for disassembly to avoid accidental separation by the user. In more detail, the raised features 7t are disposed so as to be underneath the resilient finger 8m to inhibit downward movement thereof. This therefore makes it more difficult for the stop element 8b to be slid back underneath the bridging element 4c for disassembly of the strap 2. To assist assembly of the strap 2, the raised features 7t present an inclined lead-in surface 7u.

Thirdly, the bridging element 4c includes a reinforcing rib 7v to increase robustness.

In an alternative embodiment of the invention, not shown, the strap for the dust cap 5 is made from an elastic stretchable material, for example knitted elastic. In this embodiment, the strap can be elastically extended to permit the user to remove or reapply the dust cap 5 and its flexibility allows the dust cap 5 to be easily positioned clear of the mouthpiece 3 whilst the pMDI is in use.

In a third embodiment of the invention, shown in FIGS. 4A and 4B, the dust cap 5 has elongated sides 13 which are disposable on opposed sides of the lateral section 1b of the housing 1. A pin 16 is provided on each side of the housing lateral section 1b. Each elongated side 13 of the dust cap 5 has a slot 15 along its length, which has closed ends. The slots 15 hold the pins 16 captive. The arrangement of the slots 15 and pins 16 secures the dust cap 5 to the housing 1, whilst permitting the dust cap 5 to be rotated about the common axis A-A of the pins 16 and moved towards and away from the mouthpiece 3 along the length of the slots 15.

To remove the dust cap 5, the user pulls it away from the mouthpiece 3, sliding the pins 16 within the slots 15. The user then rotates the dust cap 5 about the pins 16, swinging it below the housing 1 to prevent it obstructing the mouthpiece 3. The dust cap 5 is then reapplied by swinging it back into a position in front of the mouthpiece 3 and then sliding it back over the pins 16 until it engages the mouthpiece 3.

Figure 5:
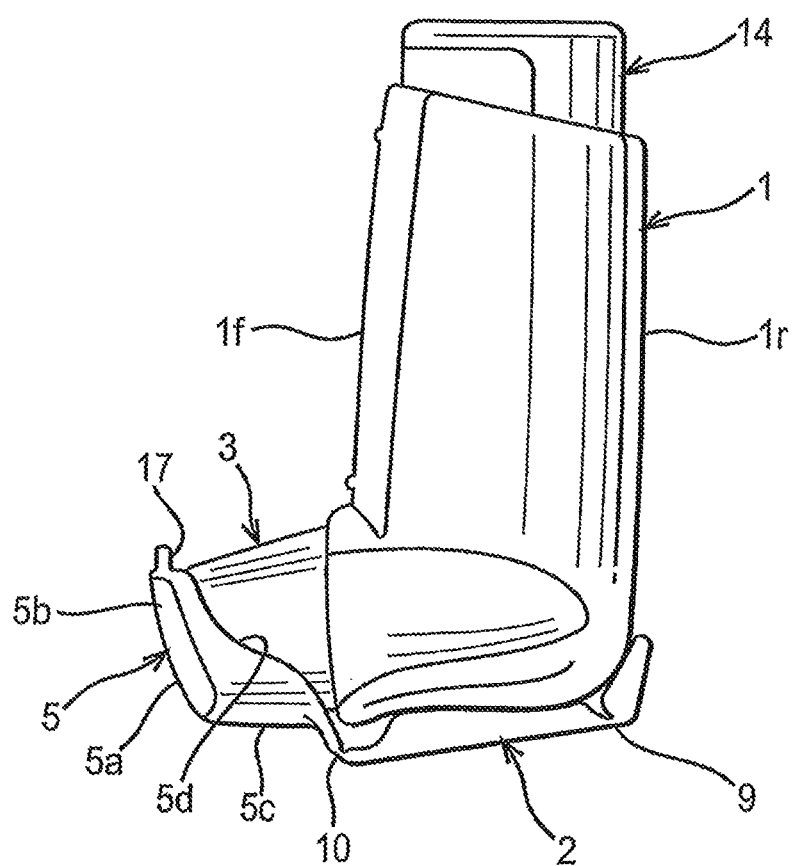
FIG. 5 shows a prior art strap for attaching a dust cap to the housing of a pMDI usable in the implementation of the invention.

Referring to FIG. 5, there is shown a pMDI with a dust cap 5 attached to the housing 1 using a prior art strap 2, having fold lines 9, 10 at each end to permit the strap and dust cap 5 to be folded behind the housing when the pMDI is in use. The sides and roof of the dust cap 5 may be cut away, leaving a lip 17 with which the dust cap 5 engages the mouthpiece 3, as described in the 'Background of the Invention' section supra. In an embodiment of the invention, the dust cap 5 of this prior art arrangement is provided with a restricting member, such as illustrated and described herein. However, this embodiment is disadvantageous compared to others for the reasons discussed above in the 'Background of the Invention' section.

Figure 6:
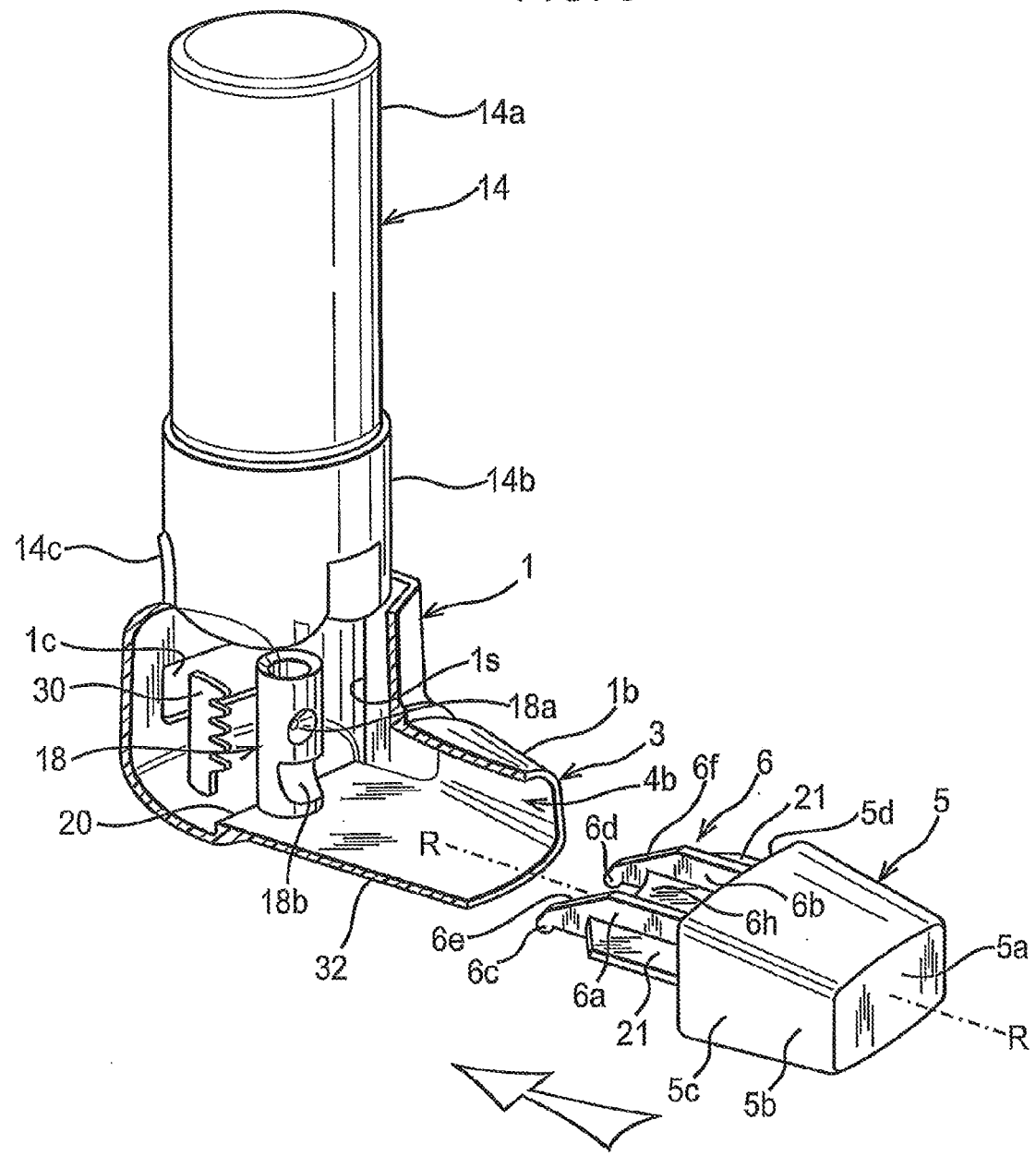
FIG. 6 shows a further embodiment of the present invention, wherein a dust cap is provided with a restricting member that comprises a pair of arms, configured as a clip to engage a step in the base of the housing of a pMDI.
Figure 6A:
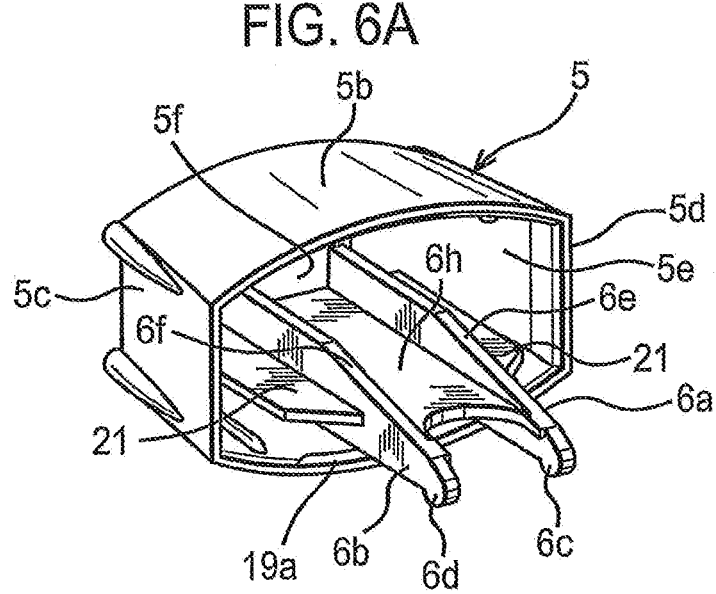
FIGS. 6A-6E are respectively perspective, plan, cross-sectional, side and front views of the dust cap in FIG. 6.
Figure 6B:
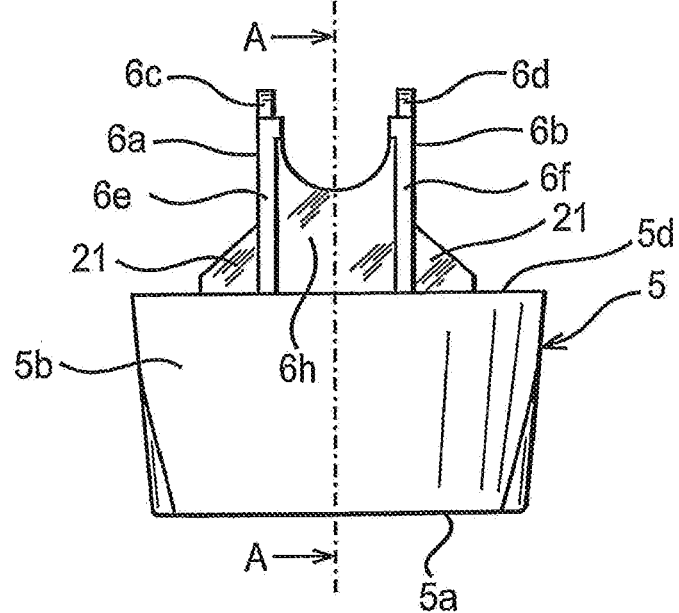
Figure 6C:
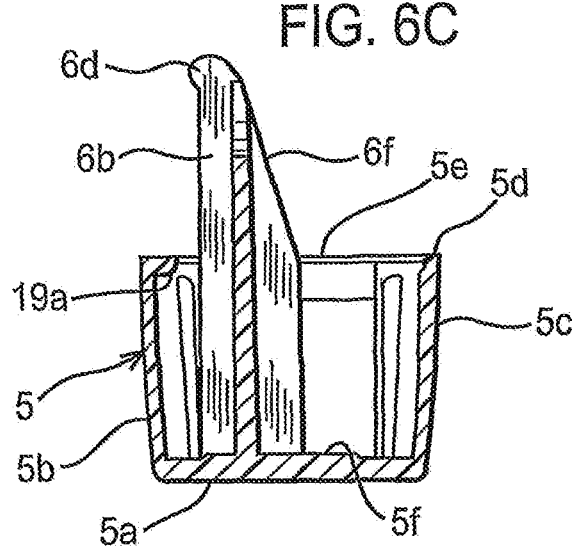

FIG. 6 is a schematic view of a pMDI in accordance with a fourth embodiment of the present invention which corresponds closely to the second embodiment described with reference to FIGS. 3A-3J. In FIG. 6 a scrap detail of the lower part of the housing 1 is shown to reveal the base surface in which the step 20 is formed and from which the stem block 18 for the valve stem (118, FIG. 6F) projects upwardly. As further shown, the stem block 18 has a spray orifice 18a oriented towards the lower open end 4b in the mouthpiece 3 whereby the metered dose fired from the canister unit 14 on depression thereof into the housing 1 is directed out of the mouthpiece 3.

FIG. 6 further shows the dose counter module 14b mounted on the leading (valve) end of the canister unit 14. The dose counter module 14b has a display window 14c which displays the number of metered doses of the medicament formulation left in the canister 14a, as described in WO-A-2004/001664 supra. The housing 1 has a cut-out or window 1c through which the patient can see the dose counter display 14c.

As detailed in WO-A-2004/001664, the dose counter module 14b has a counting mechanism which is driven through a rack-and-pinion mechanism. FIG. 6 shows the rack 30 which also projects upwardly from the housing base surface. The rack is slidingly received in an aperture (not shown) in the leading face of the dose counter module 14b. When the canister unit 14 is depressed into the housing 1 for opening of the metering valve, the rack drives a pinion (not shown) in the dose counter module 14b and the rotary movement of the pinion causes the counting mechanism to decrement the number displayed in the dose counter window 14c by dose counter wheels (not shown).

In the fourth embodiment of the invention the pMDI has a dust cap 5 for detachably engaging the mouthpiece 3 which corresponds to that shown in FIGS. 3A-3J other than that it does not include a connector or strap for connecting the cap 5 to the housing 1. Different views of the dust cap 5 of the fourth embodiment are shown in FIGS. 6A-6E.

As shown in FIGS. 6A-6E, the arms 6a, 6b forming the restricting member 6 are interconnected along part of their length by a strengthening rib 6h, in order to increase their strength and rigidity. As discussed previously, the configuration of the free ends of the arms 6a, 6b as clips 6c, 6d which engage the step 20 is advantageous, since if the canister unit 14 is moved downwards in the housing 1, for instance if the pMDI is dropped, it pushes the arms 6a, 6b towards the step 20, so as to increase the gripping force of the clips 6c, 6d to ensure that the dust cap 5 and restricting member 6 do not eject from the mouthpiece 3.

FIG. 6F shows schematically how the restricting member 6 prevents actuation of the pMDI in the same way described for the second embodiment with reference to FIG. 3F. Specifically, the arms 6a, 6b sit underneath the dose counter module 14b to prevent it moving towards the base 32 of the housing 1 the required distance for the valve stem 118 to be depressed into the canister 14a for release of the metered dose nor for the rack 30 to drive the pinion for decrementing the dose counter display 14c.

As further shown in FIG. 6F, a clip 19a is provided on the dust cap 5 to engage a slot 19b on the outer surface of the mouthpiece 3 to provide additional retention of the dust cap 5 on the housing 1. However, none of the clips 6c, 6d, 19a prevent the dust cap 5 from being fairly easily removed from the housing 1 by a user.

The restricting member 6 is asymmetrically arranged in the dust cap 5, inasmuch as being located closer to the cap bottom than to the cap top (FIGS. 6A, 6C, 6D, 6F). If the dust cap 5 is mounted on the mouthpiece 3 in an inverted orientation, then the canister unit 14 may not be able to be inserted properly into the housing 1. Accordingly, the dust cap 5 may be provided with indicia indicating the correct orientation of the cap 5, for example by providing indicia on the cap outer surface, for instance on its front face 5a.

The restricting member 6 is also provided with lateral alignment ribs (wings) 21 to prevent it from being inserted at more than a prescribed angle to the mouthpiece 3, whereupon one of the arms 6a, 6b might be inserted into a hollow 18b in the stem block 18 or be otherwise obstructed by the components of the pMDI. In other words, the alignment ribs 21 help to ensure that the dust cap 5 is mounted on the mouthpiece 3 so that the arms 6a, 6b straddle the stem block 18 with the clips 6c, 6d clipping into engagement with the step 20.

In an alternative embodiment of the invention, not shown, the clips 6c, 6d of the restricting member 6 could be reconfigured such that they clip onto the stem block 18 to retain the cap 5 in place for blocking movement of the canister unit 14 in the housing 1 in the firing direction.

In a further alternative embodiment, not shown, the clips 6c, 6d of the restricting member 6 could be replaced with laterally extending clips which, when the dust cap 5 is mounted on the mouthpiece 3, clip behind a sidewall is (FIG. 6) in the housing 1. Such lateral clips could also be used in conjunction with the clips 6c, 6d.

Figure 6D:
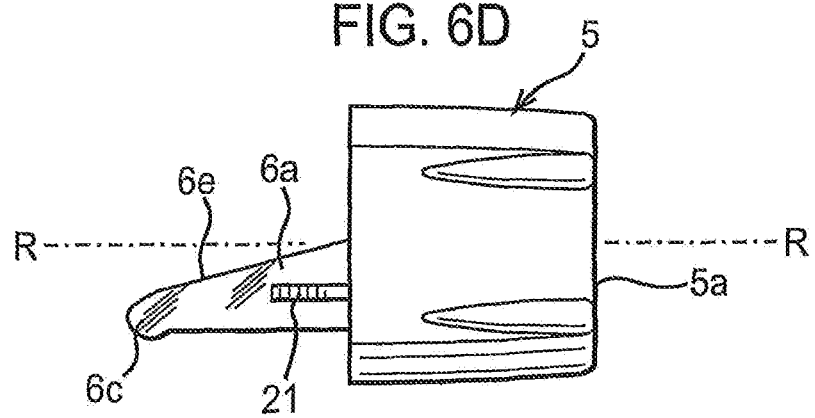
Figure 6E:
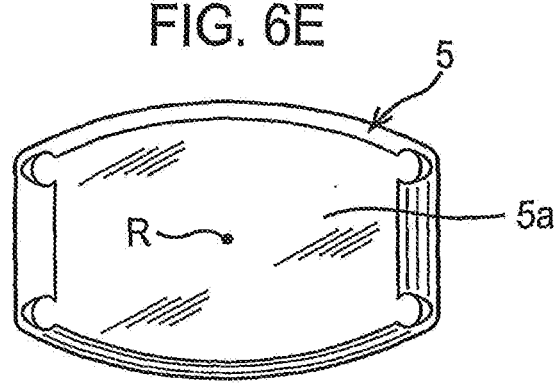
Figure 6F:
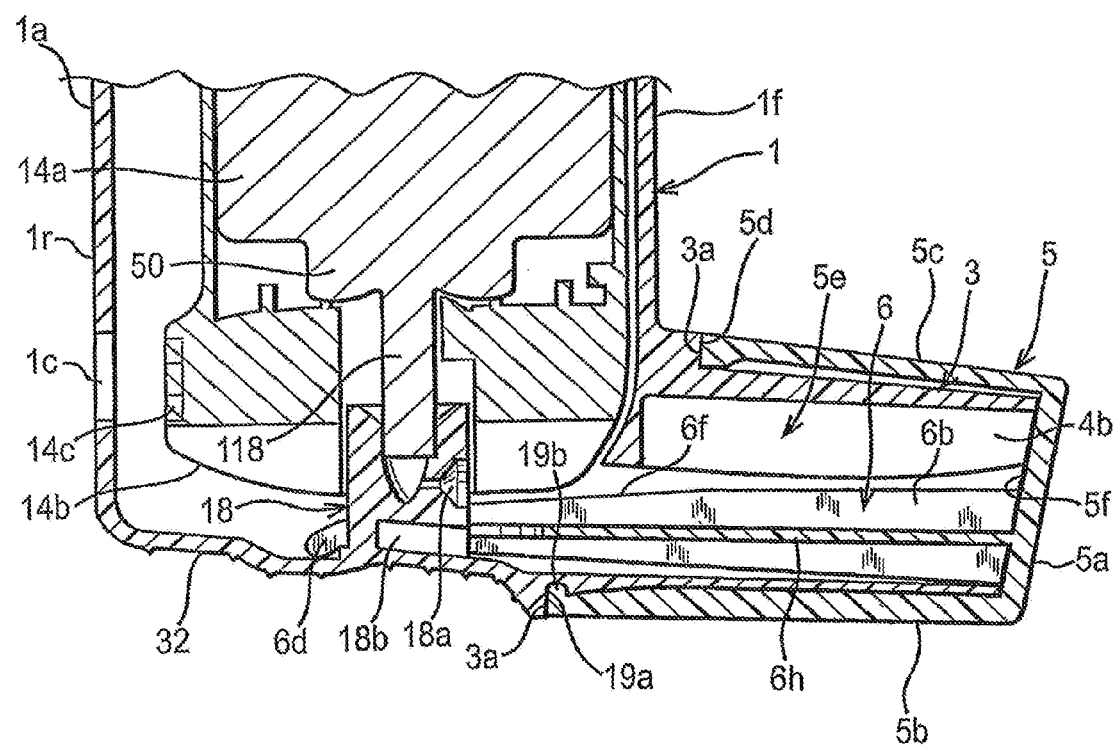
FIG. 6F is a schematic, fragmentary, part sectional view of the dust cap and canister unit of the pMDI of FIG. 6 assembled to the housing showing how the restricting member is positioned in the housing relative to the canister unit.
Figure 6G:
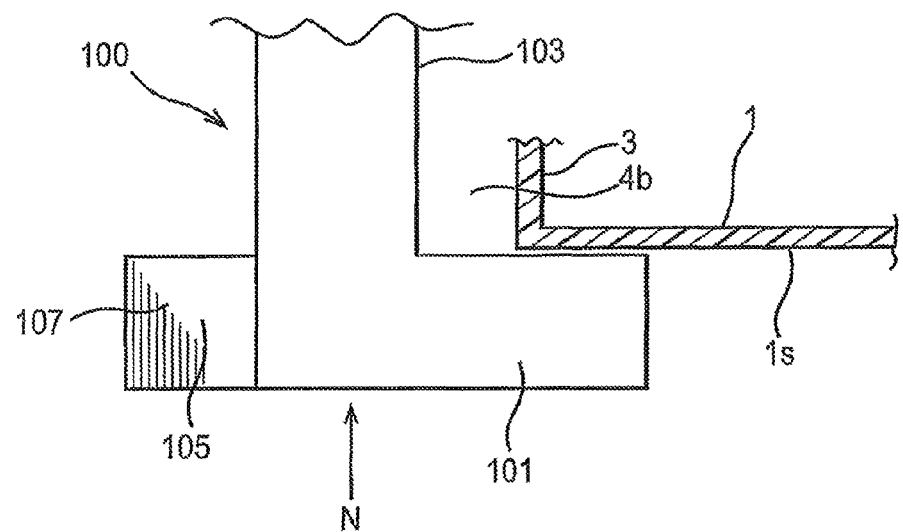
FIGS. 6G and 6H are schematic views of a modification that may be incorporated in the embodiment of FIGS. 6-6F.
Figure 6H:
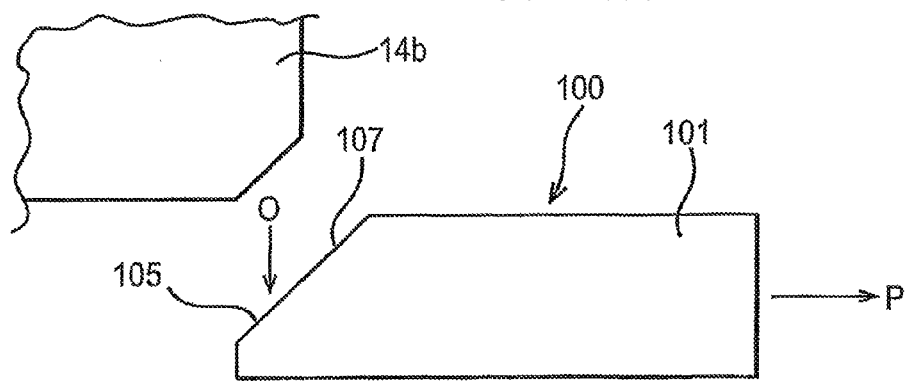

In another alternative embodiment, shown in FIGS. 6G and 6H, in addition to the restricting member 6, the dust cap 5 of FIGS. 6-6F is provided with a pair of supplementary clips 100, only the clip end 101 of one of the clips 100 being shown in FIGS. 6G and 6H. FIG. 6G is a plan view of the clip end 101, while FIG. 6H is an end view on arrow N in FIG. 6G.

The clips 100 have resilient legs 103 which extend outwardly from the dust cap 5 on different sides of the central axis R-R (FIG. 6). As will be understood from FIG. 6G in conjunction with FIG. 6, when the dust cap 5 is mounted to the mouthpiece 3, the clips 100 extend through the opening 4b and the resilient legs 103 bias the clip ends 101 outwardly so they clip behind the sidewall 1s of the housing 1.

The clip ends 101 of the clips 100 are further provided with an extension 105 having an inclined surface 107. As shown in FIG. 6H, the extensions 105 are configured and arranged to dispose the inclined surfaces 107 underneath the dose counter module 14b. If the canister unit 14 is moved downwardly in the housing 1 while the dust cap 5 is mounted on the mouthpiece 3, as indicated by arrow O in FIG. 6H, the leading end of the dose counter module 14b will engage the inclined surfaces 107 and bias the clip ends 101 in the direction of arrow P resulting in the clip ends 101 clipping even more firmly behind the sidewall 1s of the housing 1. Thus, the clips 100 provide supplementary protection against the dust cap 5 being ejected from the mouthpiece 3 by downward movement of the canister unit 14 in the housing 1, e.g. caused by the user or dropping of the pMDI.

If desired, the clips 100 could be used as a restricting member in their own right, that is to say, in place of the restricting member 6. The clips 100 could also be used as a supplement to a restricting member which does not incorporate clips, for instance with the restricting member 6 of FIGS. 6-6F where the restricting member 6 is not provided with the clips 6c, 6d.

Figure 7A:
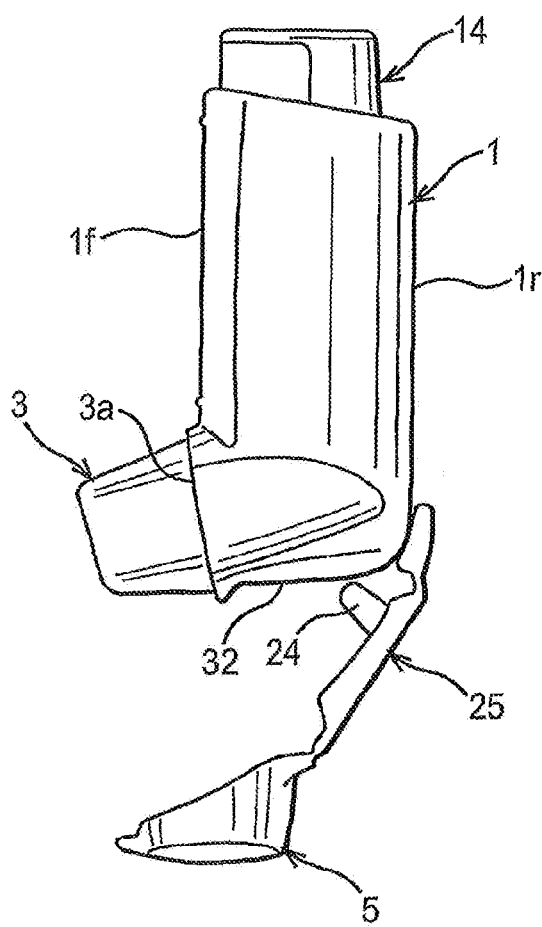
FIGS. 7A and 7B show yet another embodiment of the present invention, having a dust cap secured to the housing of a pMDI by a strap and a restricting member attached to the strap and capable of entering the housing through a hole in its base.
Figure 7B:
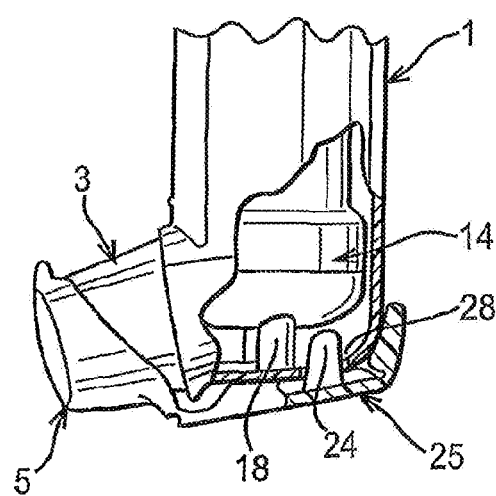

FIGS. 7A and 7B show a pMDI in accordance with a fifth embodiment of the present invention in which a strap 25 is provided to attach the dust cap 5 to the housing 1 and a restricting member 24 is mounted on said strap. The strap 25 and restricting member 24 are positioned so that when the dust cap 5 is in a position in which it engages the mouthpiece 3, the restricting member 24 protrudes into the housing 1 through a hole 28 in the base 32 of the housing 1 to act as a prop for the canister unit 14. The length of the restricting member 24 is such that it prevents the canister unit 14 from being depressed to within a predetermined distance of the base 32 of the housing 1 to prevent actuation (firing and counting) of the pMDI. When the dust cap 5 is removed, the strap 25 moves away from the base 32 of the housing 1 and the restricting member 24 exits the hole 28 thereby enabling the canister unit 14 to be actuated.

FIGS. 8A and 8B show a pMDI in accordance with a sixth embodiment of the present invention in which a disposable restricting member 22 is removably inserted between the housing 1 and the canister unit 14. The restricting member 22 is made from an elastically compressible material, such as a foam, and is inserted at the upper open end 4a of the housing 1 with the canister unit 14 positioned in a rest position in the housing 1 from which it needs to be depressed into the housing for operation of the dose counter module 14b and the metering valve 50. The restricting member 22 acts as wedge between the canister unit 14 and the inner surface of the housing 1 and also tilts the canister unit 14 in the direction of arrow C into engagement with the housing inner surface. As the restricting member 22 is elastically compressible, it applies an outward lateral holding force on the inner surface of the housing 1 and the outer surface of the canister unit 14. Depression of the canister unit 14 into the housing 1 for actuation of the metering valve 50 and the dose counter module 14b is thereby prevented.

Unlike the previous embodiments hereinabove described with reference to the FIGURES of drawings, the restricting member 22 in the sixth embodiment also prevents or inhibits retraction of the canister unit 14 from the housing 1 until the restricting member 22 is removed.

As represented in FIG. 8B, the restricting member 22 is removed and discarded prior to the first actuation of the pMDI. It is particularly useful for preventing inadvertent actuation of the pMDI before the pMDI is given to the patient, e.g. through knocks when being shipped or transported from the manufacturer to the distributor and then to the clinic.

The restricting member 22 may be adhesive, to further increase the holding force it applies to the canister unit 14 and the housing inner surface.

The wedge concept for the restricting member may also be realised in other shapes and configurations for the restricting member 22.

FIGS. 9A and 9B show a seventh embodiment of the invention in which an annular restricting member 22 is slid over the canister 14a to form a tight fit thereon, e.g. an interference or press fit. This is achieved by the restricting member 22 having an aperture 22a of transverse dimension which is no greater than that of the canister 14a and, where the aperture 22a is of a transverse dimension less than that of the canister 14a, being radially expandable when slid onto the canister 14a. The restricting member 22 prevents depression of the canister unit 14 into the housing 1 far enough for actuation of the metering valve 50 and the dose counter module 14b by abutting with the lip 4c of the upper open end 4a of the housing 1. In this embodiment, the restricting member 22 is in the form of a foam collar, although other elastic or resilient materials would work equally well.

Figure 10A:
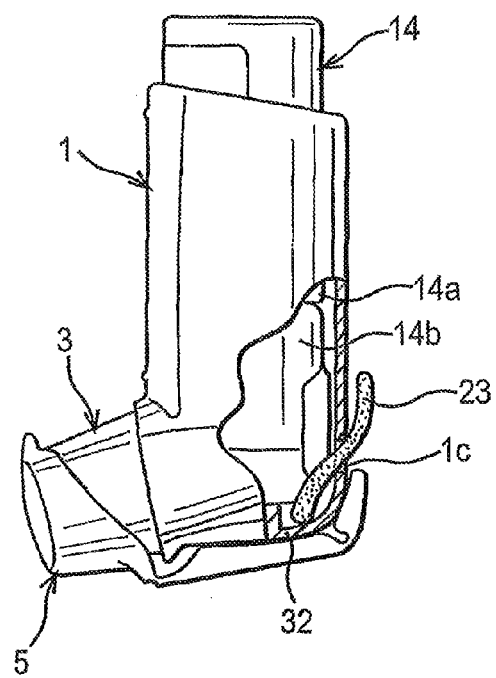
FIGS. 10A and 10B show an embodiment of the present invention having a restricting member inserted between a canister unit and the housing of a pMDI, through a display window in the housing.
Figure 10B:
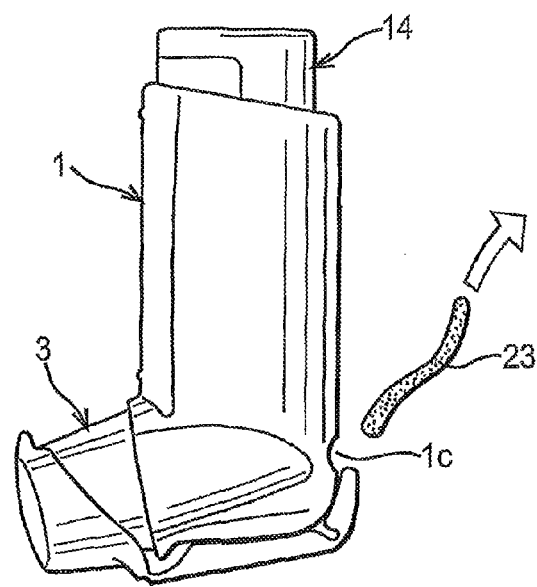

FIGS. 10A and 10b show an eighth embodiment of the present invention wherein the pMDI is packaged with a restricting member 23 partially inserted into the housing 1 through the display window 1c. The user removes and discards the restricting member 23 from the housing 1 prior to the first actuation of the pMDI. When in place, the restricting member 23 separates the canister unit 14 and the base 32 of the housing 1. This prevents the canister unit 14 from moving sufficiently far inside the housing 1 for actuation of the metering valve 50 and the dose counter module 14b. As shown in FIG. 10b, the user removes the restricting member 23 by pulling on the portion that remains exterior to the housing 1. With the restricting member 23 removed, the canister unit 14 is free to move inside the housing 1 for actuation of the pMDI.

In accordance with the invention, which may be considered a variant of the sixth and/or eighth embodiments, a discardable restricting member (not shown) may be positioned underneath the canister unit 14 so as to space the canister unit 14 from the base surface of the housing 1 so that the canister unit 14 is unable to be depressed far enough for actuation and counting. The restricting member may of the same material as in the sixth embodiment. The restricting member extends through the mouthpiece 3 and optionally may be releasably attached to a dust cap 5, e.g. through a temporary adhesive. The restricting member is removed by a user before first actuation of the inhaler by removing the dust cap 5 which either pulls the restricting member out of the housing 1 through the mouthpiece 3 or subsequently allows the user to pull the restricting member out of the opened mouthpiece 3 by pulling on the free end of the restricting member located in, or protruding from, the mouthpiece 3. In the former case, the user subsequently removes the restricting member from the dust cap so that it can be discarded. The restricting member may be of elongate form and may be sized to extend into the space between the stem block 18 and the rack 30, e.g. so as to be wedged between the stem block 18 and the rack 30. It will be appreciated that the dust cap 5 need not be provided with its own restricting member.

FIGS. 11A and 11B show a ninth embodiment of the invention in which an adhesive restricting member 33 adheres to the canister unit 14 through the housing display window 1c. The restricting member 33 is an adhesive tape that also adheres to the housing 1. Securing the canister unit 14 and the housing 1 together in this manner prevents relative movement between the two such that the canister unit 14 can be neither actuated (firing and counting) nor removed. Prior to first use, the patient peels the restricting member 33 away and discards it, as shown in FIG. 113.

Figure 12A:
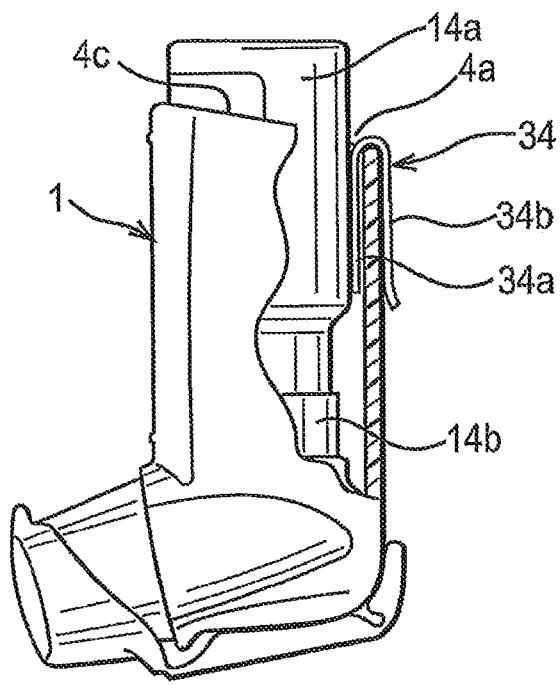
FIGS. 12A and 12B show an alternative of the embodiment of FIGS. 11A and 11B.
Figure 12B:
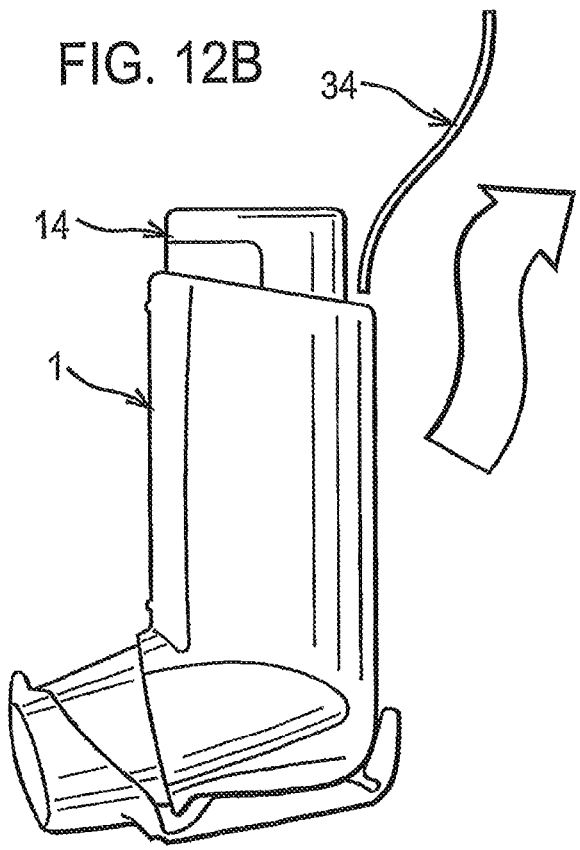

FIGS. 12A and 123 show a tenth embodiment of the invention having an adhesive restricting member 34 in the form of a double-sided adhesive tape which is folded over the lip 4c of the upper open end 4a of the pMDI housing 1 to define an inner tape section 34a, which is adhered to the outer surface of the canister unit 14, and an outer tape section 34b, which is adhered to the outer surface of the housing 1. The inner tape section 34a may also be adhered to the inner surface of the housing 1. As will be appreciated, this configuration prevents depression of the canister unit 14 into the housing 1 for actuation (firing and counting) thereof. The restricting member 34 is removed and discarded by the patient prior to first use of the pMDI.

Figure 13A:
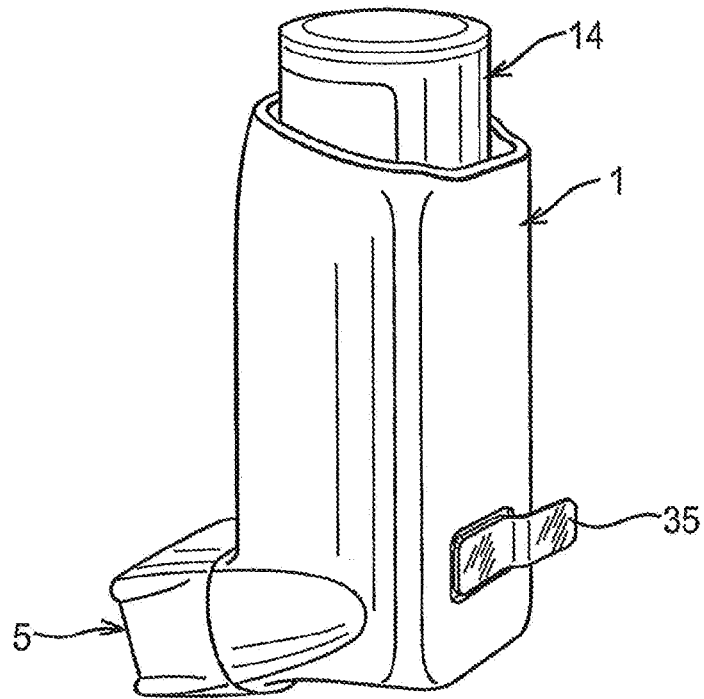
FIGS. 13A and 13B show an embodiment of the invention in which a restricting member is adhesively secured to the canister unit of a pMDI through a window in the housing.
Figure 13B:
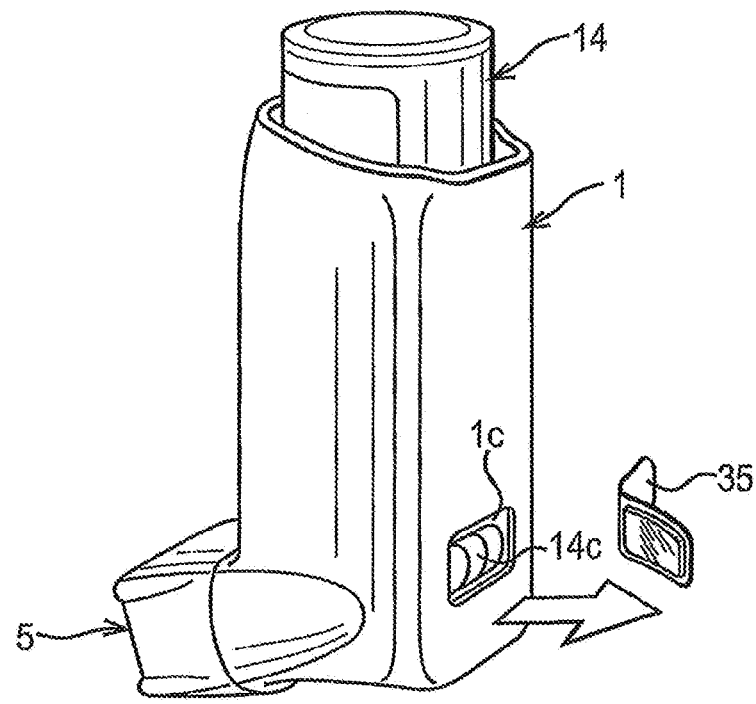

FIGS. 13A and 13B show an eleventh embodiment of the invention which is similar to the ninth embodiment in having a restricting member 35 that is adhered to the canister unit 14 through the housing display window 1c. In this instance, however, the restricting member 35 is not adhered to the housing 1. The restricting member 35 is an adhesive pad of not negligible thickness, preferably at least the thickness of the housing 1 around the display window 1c, which is aligned adjacent the edge of the display window 1c. The canister unit 14 is prevented from moving downwards and upwards in the housing 1 for actuation and removal thereof by the blocking action of the restricting member 35 against the edge of the display window 1c. Again, the restricting member 35 is removed and discarded prior to the first actuation of the pMDI, as indicated in FIG. 13B.

Figure 14A:
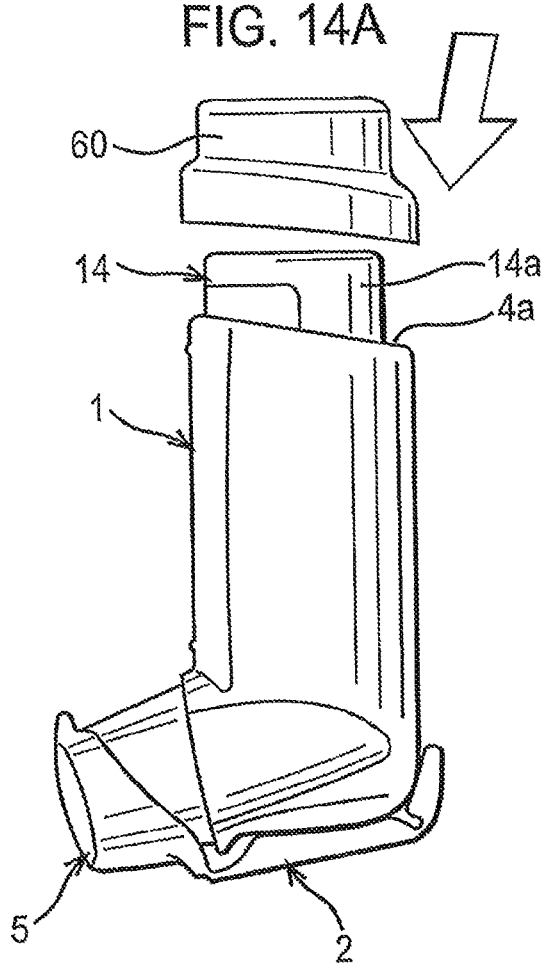
FIGS. 14A and 14B show a further embodiment of the invention in which a restricting member is mounted on the trailing end of the canister unit of a pMDI.
Figure 14B:
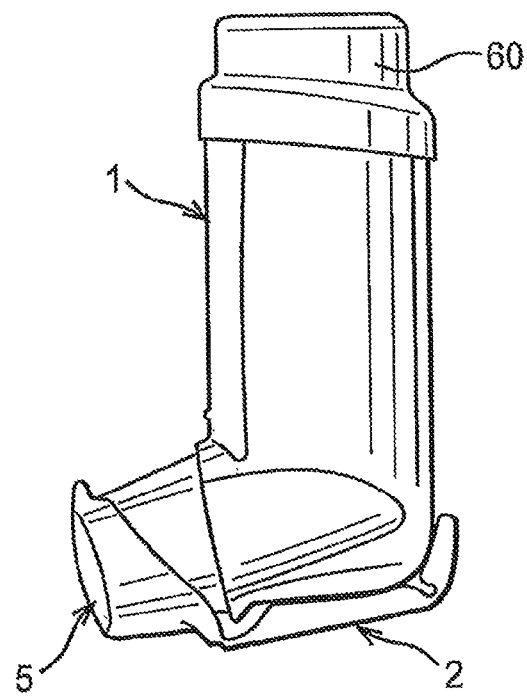

FIGS. 14A and 14B show a twelfth embodiment of the invention in which a restricting member 60 in the form of a cap is press-fitted to both the top of the canister unit 14 and the outer surface of the housing 1 adjacent its upper open end 4a. The cap may be formed by vacuum forming. Relative movement of the canister unit 14 in the housing 1 is thus prevented insofar as stopping actuation (firing and counting) and removal of the canister unit 14.

Figure 15A:
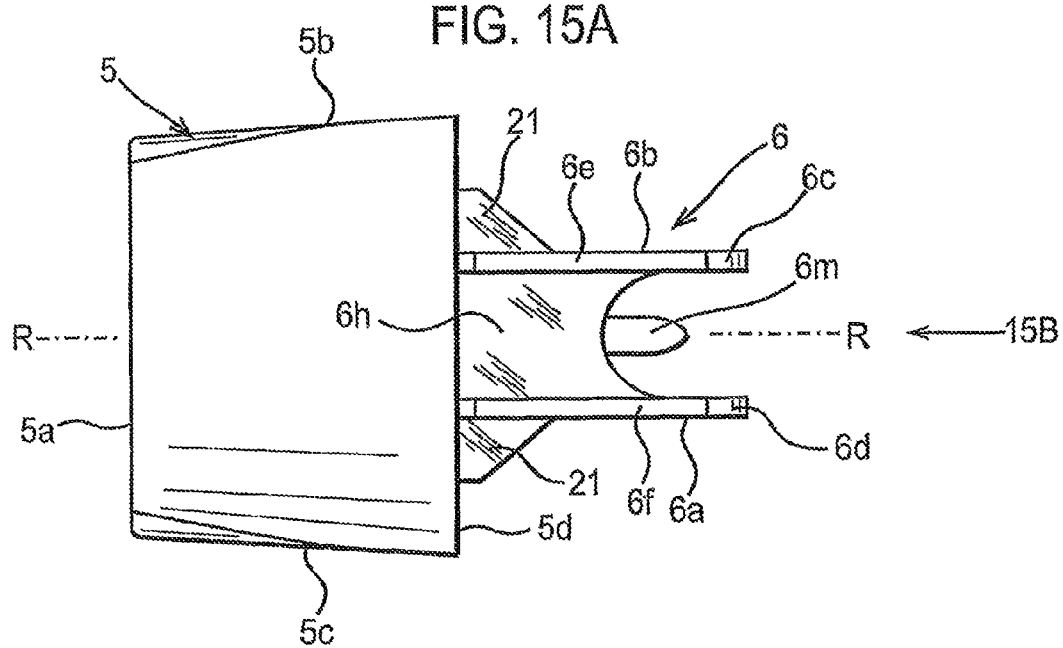
FIGS. 15A and 15B show another embodiment of the invention which corresponds to that shown in FIGS. 6-6F other than being provided with guide means to guide a user to mount the dust cap in the correct orientation on the dispensing outlet of a pMDI.
Figure 15B:
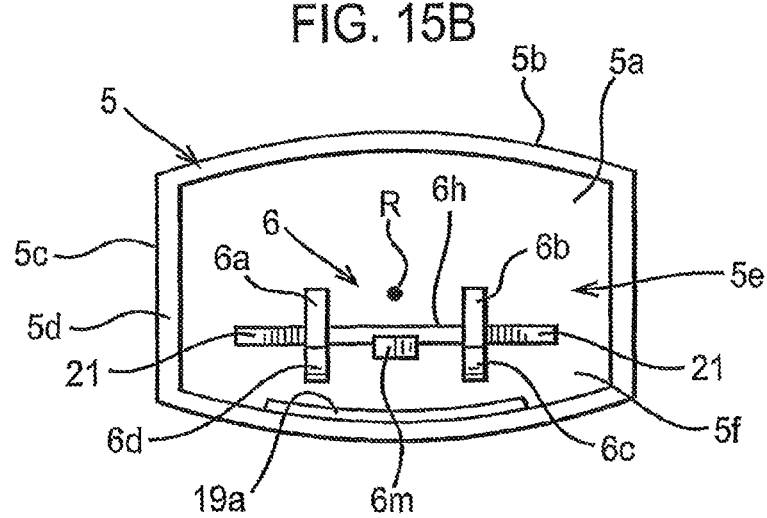

FIGS. 15A and 15B respectively show plan and front views of a dust cap 5 in accordance with a thirteenth embodiment of the invention which corresponds in nearly all respects to the dust cap 5 in the fourth embodiment shown in FIGS. 6-6F. The only difference of note is that the asymmetrically mounted restricting member 6 is further provided with a middle arm 6m projecting from the strengthening rib 6h between the outer arms 6a, 6b, thereby forming a trident configuration. The length of the middle arm 6m is shorter than the outer arms 6a, 6b.

In common with the first to fourth embodiments, the dust cap 5 of the thirteenth embodiment has a hollow body 5b which is of a shell form and a generally rectangular cross-sectional shape. The body 5b comprises the front face 5a and a side skirt 5c. The rear end of the side skirt 5c presents an annular lip 5d about a mouth 5e to the inner volume of the body 5b.

The restricting member 6 extends rearwardly from an inner surface 5f of the front face 5a.

The mouthpiece 3 of the pMDI housing 1 is of complementary shape and size to the cap body 5b whereby the cap body 5b is slidable rectilinearly over the mouthpiece 3 as a push-fit. It will also be appreciated that the mutual shapes of the cap body 5b and the mouthpiece 3 ensure that the cap 5 is non-rotatable on the mouthpiece 3.

Noting the respective shapes of the cap body 5b and the mouthpiece 3, in the fourth embodiment the cap body 5b is able to be push-fit onto the mouthpiece 3 in two different orientations of the cap 5 about its central axis R-R. In a first, correct orientation, in which the restricting member 6 is underneath the central axis R-R, as shown in FIGS. 6 and 6D, for example, the cap 5 is able to be push-fit onto the mouthpiece 3 so that the clips 6c, 6d clip to the step 20, as previously described. Moreover, as will be understood from FIG. 6F, for example, the annular lip 5d of the side skirt 5c abuts an annular surface 3a of the pMDI housing 1 about the mouthpiece 3 so that there is no gap therebetween. In this position the clips 19a, 19b will also clip together.

However, if the cap 5 is turned upside-down (i.e. rotated 180° about the central axis R-R) from the first, correct orientation to a second, incorrect orientation, so that the restricting member 6 is disposed above the central axis R-R, the cap 5 is still able to be push-fit onto the mouthpiece 3 so that the annular lip 5d abuts the annular housing surface 3a since the arms 6a, 6b of the restricting member 6 will straddle the stem block 18 and the strengthening rib 6h will be spaced from the stem block 18. Nonetheless, none of the clips 6c, 6d, 19a of the cap 5 will clip to their respective counterparts. Accordingly, the cap 5 will not be secured to the mouthpiece 3 as well as if in the first, correct orientation. Moreover, since there would be no gap between the annular lip 5d and the annular housing surface 3a, the user is not given an indication that the cap 5 is not correctly fitted on the mouthpiece 3.

There is therefore a possibility that the cap 5 could inadvertently detach from the mouthpiece 3, for instance if a downward pressure is applied to the base of the canister 14a since the leading end of the dose counter module 14b will tend to push the cap 5 outwardly by acting on the upside-down restricting member 6.

The cap 5 of the thirteenth embodiment is adapted to alleviate this possibility through the provision of the middle arm 6m, as will be described in more detail with reference to FIGS. 16A-D.

Figure 16A:
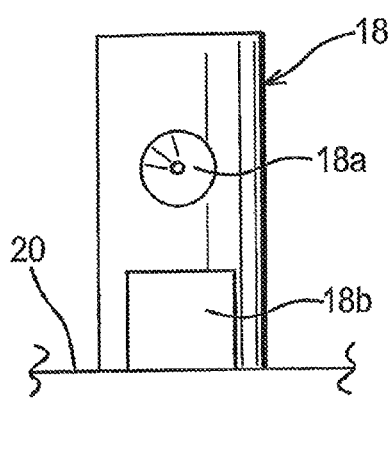
FIGS. 16A-16D illustrate how the guide means of the embodiment of FIGS. 15A and 15B operate.
Figure 16B:
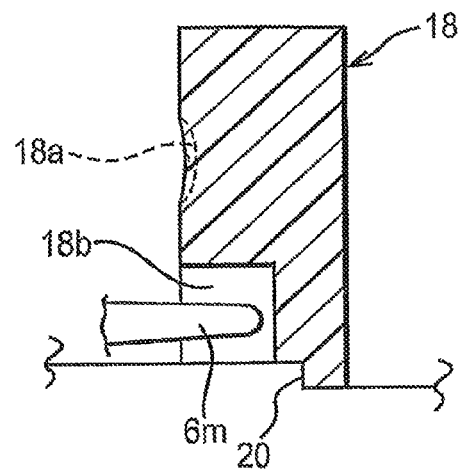

FIG. 16A is an enlarged front view of the stem block 18 shown in FIGS. 6 and 6F. FIG. 16B schematically shows that, when the dust cap 5 of the thirteenth embodiment is in its correct angular orientation about its central axis R-R, as shown in FIG. 15B, the middle arm 6m of the restricting member 6 slides into the hollow 18b in the stem block 18 underneath the spray orifice 18a so as not to interfere with the push-fit mounting of the cap 5 on the mouthpiece 3 so that the clips 6*c*, 6*d* engage the step 20 and the clips 19*a*, 19*b* engage. Moreover, the annular cap body lip 5*d* will form a flush fit with the annular housing surface 3*a*.

Figure 16C:
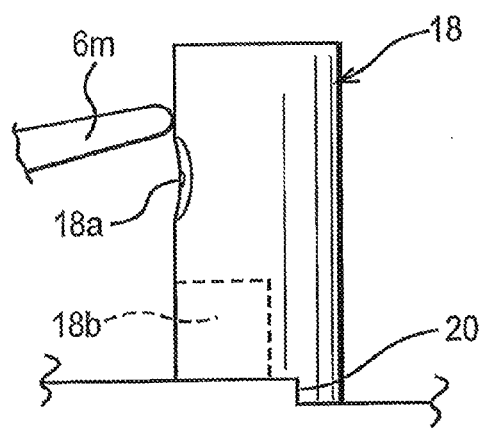
Figure 16D:
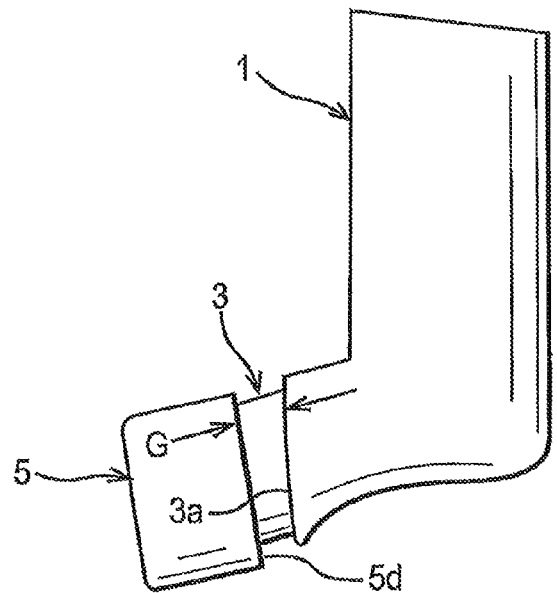

On the other hand, FIG. 16C shows that if an attempt is made to mount the cap 5 on the mouthpiece 3 in the incorrect upside-down orientation, the middle arm 6*m* will hit the stem block 18 above the hollow 18*b*. As illustrated in FIG. 16D, this will occur before the cap 5 has been pushed onto the mouthpiece 3 far enough for the annular cap body lip 5*d* to meet the annular housing surface 3*a* so that a gap G is left therebetween. The user is therefore given a tactile and visual indication that the cap 5 is incorrectly orientated, namely:— the resistance against further rectilinear movement of the cap 5 onto the mouthpiece 3 provided by the middle arm 6*m* abutting the stem block 18, and the existence of the gap G between the annular cap body lip 5*d* and the annular housing surface 3*a*.

The user will be prompted by these indications to orient the cap 5 into the correct orientation for installation on the mouthpiece 3.

Other means may be provided to prevent incorrect mounting of the cap 5 to the mouthpiece 3 additional to, or as an alternative to, the middle arm 6*m*. As an example, the cap body 5*b* may be provided with an extension which is offset to the central cap axis. R-R, for instance the same side of the central axis R-R as the restricting member 6, and which does not interfere with mounting of the cap 5 to the mouthpiece 3 in the correct or intended cap orientation, but strikes a surface of the pMDI, e.g. the housing 1, when the cap 5 is attempted to be mounted to the mouthpiece 3 in the incorrect or unintended orientation. FIGS. 17A-B and 18A-B illustrate embodiments of the invention provided with such extensions.

Figure 17A:
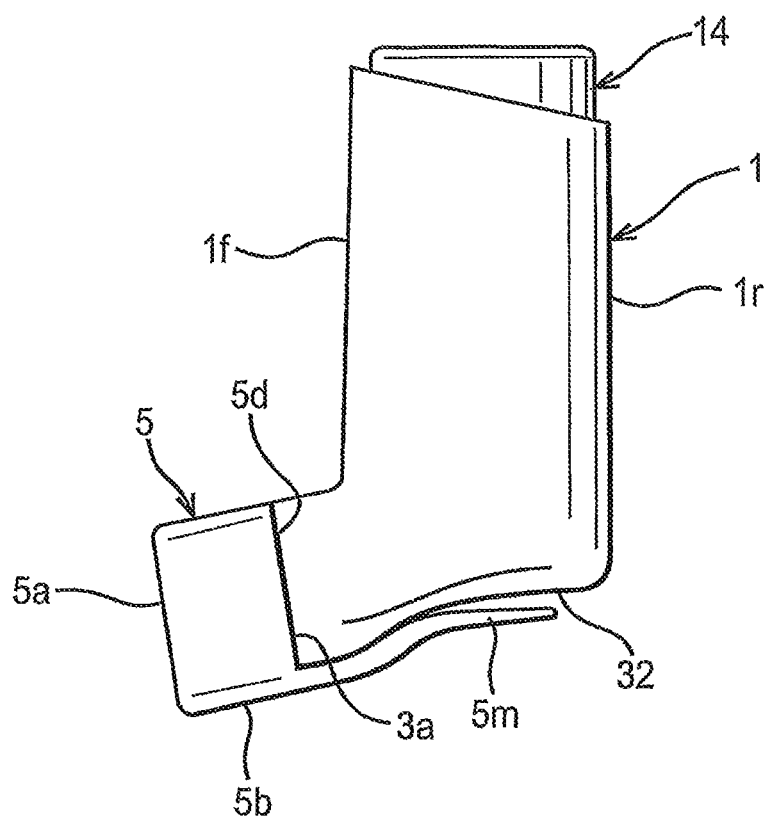
FIGS. 17A and 17B show another embodiment of a dust cap in accordance with the present invention which incorporates the same principle of operation as the embodiment of FIGS. 15A and 15B.
Figure 17B:
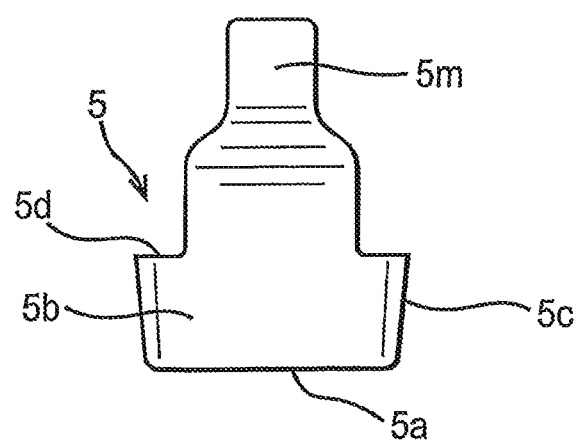

FIGS. 17A-B show a fourteenth embodiment of the invention in which the cap body 5*b* has a resilient extension 5*m* which, in this particular embodiment, takes the form of a tongue, as will be understood from the underneath view of the cap 5 in FIG. 17B. The extension 5*m* projects from the side skirt 5*c* of the cap body 5*b* and, in the correct cap orientation, slides underneath the pMDI housing 1, as shown in FIG. 17A. The extension is shaped to conform to the base 32 of the housing 1 and the resilience of the extension 5*m* biases it towards the housing base 32 so that it does not protrude from the housing 1.

As will be appreciated, the positioning and length of the extension 5*m* is such that, if an attempt is made to slide the dust cap 5 over the mouthpiece 3 in its incorrect orientation, the extension will hit a front face 1*f* of the housing 1 before the cap 5 is properly mounted on the mouthpiece 3. Again, an indication of this is given by the annular cap body lip 5*d* being spaced from the annular housing surface 3*a* when the extension 5*m* strikes the housing front face if.

Figure 18A:
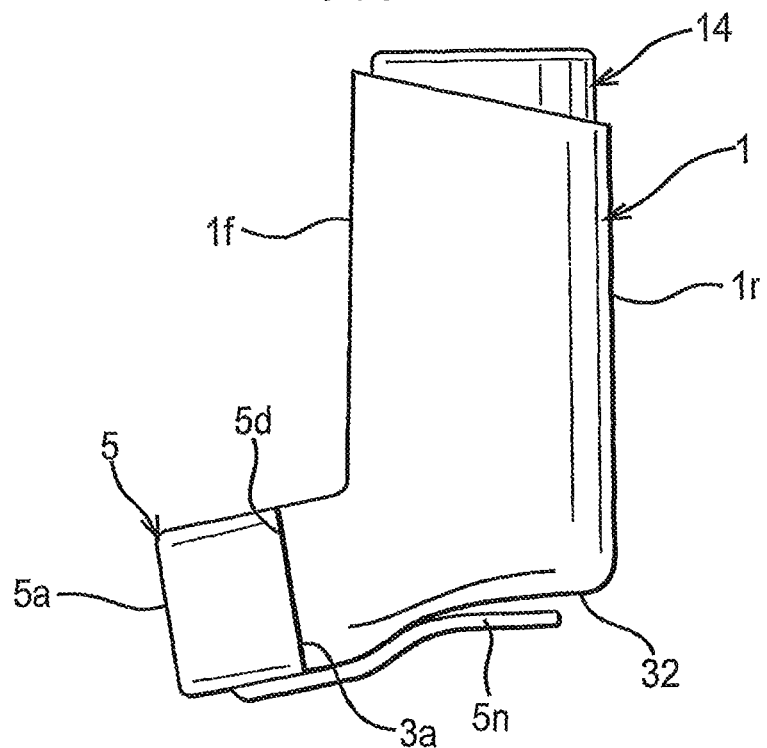
FIGS. 18A and 18B show a modification of the embodiment of FIGS. 17A and 17B.
Figure 18B:
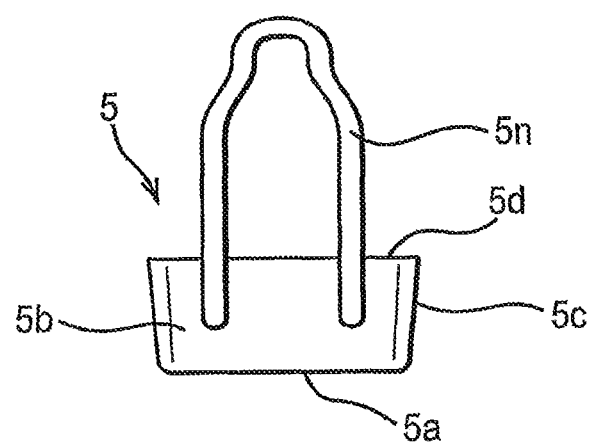

FIGS. 18A and 18B illustrate a fifteenth embodiment of the invention in which the cap 5 corresponds to that shown in FIGS. 17A and 17B other than the resilient extension being in the form of a frame 5*n*, as shown in the underneath plan view of FIG. 18B.

Figure 19A:
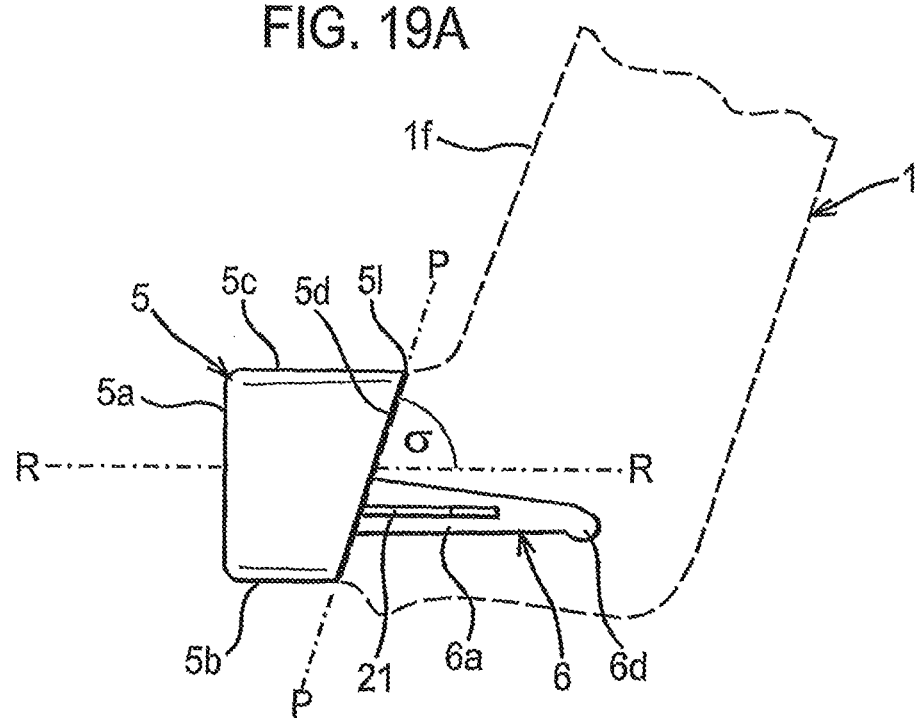
FIGS. 19A and 19B show a yet further embodiment of the invention in which a dust cap has means to prevent incorrect mounting thereof on a pMDI dispensing outlet.
Figure 19B:
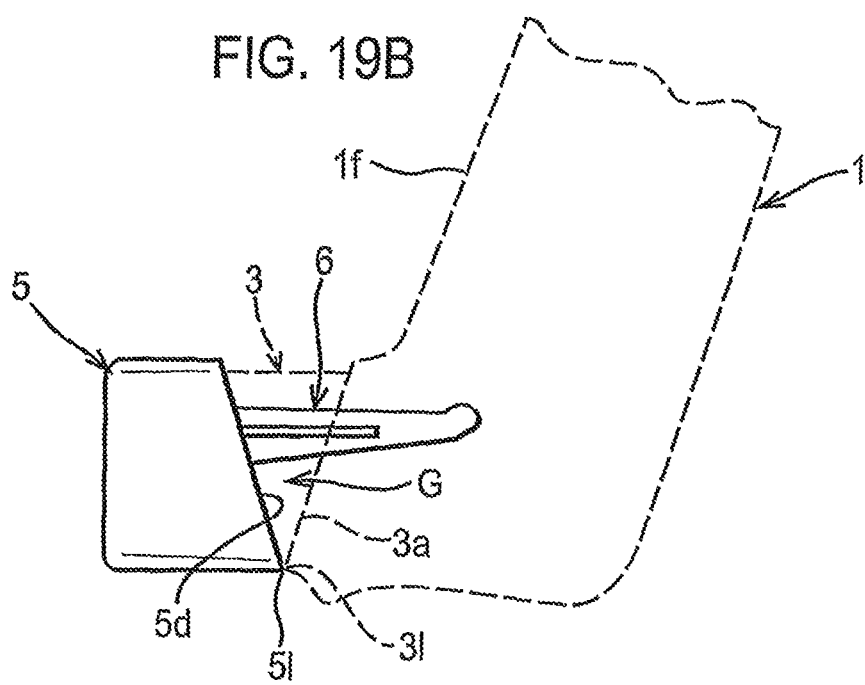

In FIGS. 19A and 19B there is shown another dust cap 5 in accordance with a sixteenth embodiment of the invention which corresponds to the fourth embodiment of FIGS. 6-6F, and optionally the thirteenth embodiment of FIGS. 15A and 15B, but where the annular cap body lip 5*d* lies on an inclined plane P-P which extends orthogonally to the central axis R-R—along which the cap 5 is translated onto the mouthpiece 3 as in the other embodiments involving use of a dust cap 5, whether with a strap or not—but which is oriented at an inclined angle σ to the central axis R-R.

The annular housing surface 3*a* is of complementary form to the annular lip 5*d* so that, when the cap 5 is oriented correctly about its central axis R-R, as shown in FIG. 19A, the cap 5 can be moved along its central axis R-R onto the mouthpiece 3 until the lip 5*d* forms a flush fit with the annular housing surface 3*a* so that there is no gap therebetween. At this point, the clips 6*c*, 6*d* of the restricting member 6 engage with the step 20 in the housing, as do the clips 19*a*, 19*b* on the cap 5 and housing 1.

However, if the cap 5 is turned upside-down, as shown in FIG. 19B, it is not possible for the annular lip 5*d* of the cap body 5*b* to form a flush fit with the annular housing surface 3*a*. The leading edge 51 of the lip 5*d* contacts the forwardmost edge 3*l* of the housing surface 3*a* leaving a gap G between the remainder of the opposing faces of the lip 5*d* and the housing surface 3*a*. The user thus has a visual indicator that the cap 5 is the wrong way up and needs to be inverted to the correct orientation for proper mounting on the mouthpiece 3.

Figure 20A:
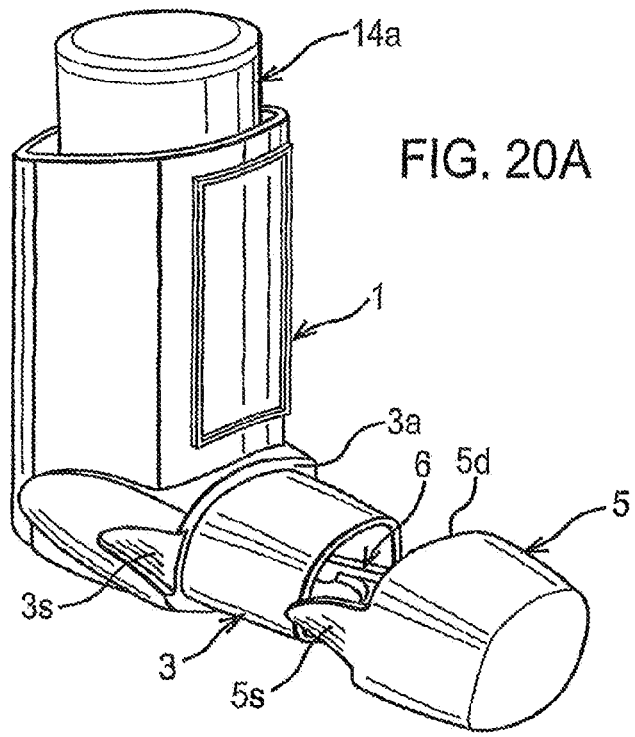
FIGS. 20A and 20B show another embodiment of the invention in which a dust cap is provided with means to prevent and/or indicate incorrect mounting thereof on a pMDI dispensing outlet.
Figure 20B:
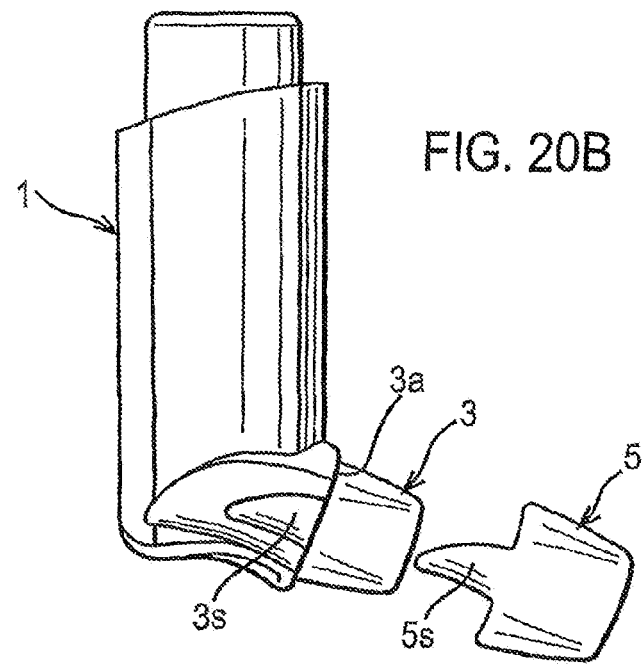

In FIGS. 20A and 20B there is shown a dust cap 5 in accordance with a seventeenth embodiment of the invention. In this embodiment, the annular cap body lip 5*d* includes a tongue section 5*s* for receipt in a complementary groove section 3*s* in the annular housing surface 3*a* about the mouthpiece 3. The groove and tongue sections 3*s*, 5*s* can only fit together when the cap 5 is pushed over the mouthpiece 3 in the correct orientation for proper placement of the restricting member 6. The tongue and groove feature guides the user to place the cap 5 on the mouthpiece 3 correctly.

In this embodiment, the groove and tongue sections 3*s*, 5*s* are asymmetric. Thus, if desired, they could be one of a pair of such sections, on diametrically opposed sides of the cap 5 and the mouthpiece 3, since they would still only be able to mate if the cap 5 were correctly oriented due to the asymmetrical nature of these sections.

Figure 21A:
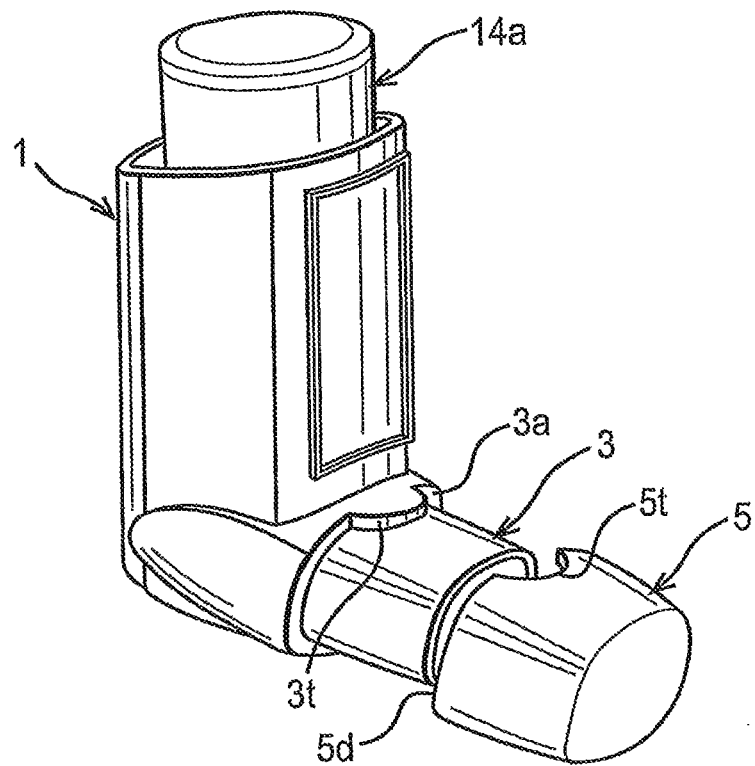
FIGS. 21A and 21B show yet another embodiment of the invention in which a dust cap is provided with means to prevent and/or indicate incorrect mounting thereof on a pMDI dispensing outlet.
Figure 21B:
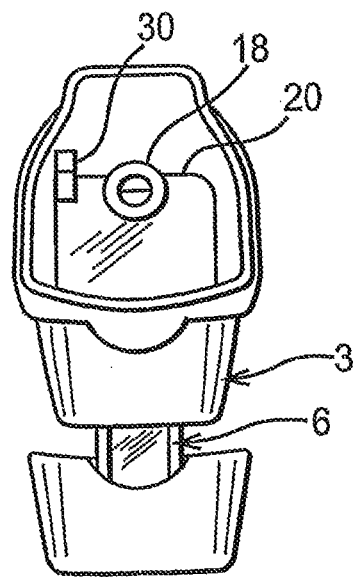

FIGS. 21A and 21B show a dust cap 5 of an eighteenth embodiment of the invention in which the annular housing surface 3*a* is provided with a tongue section 3*t*, while the cap body lip 5*d* has a complementary groove section 5*t* which is only able to receive the tongue section 3*t* when the cap 5 is pushed onto the mouthpiece 3 in the correct cap orientation.

Figure 22A:
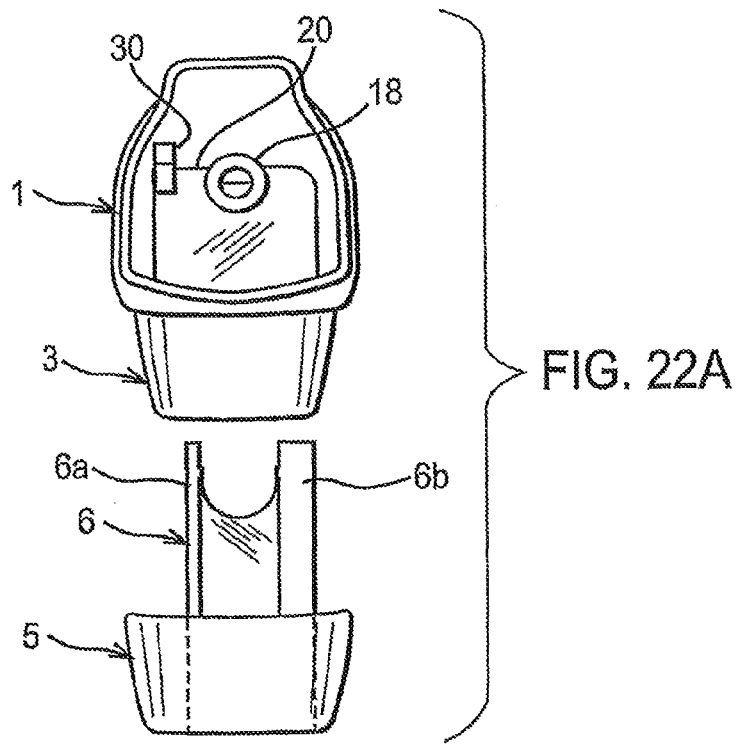
FIGS. 22A-22C show a further embodiment of the invention in which a dust cap is provided with means to prevent and/or indicate incorrect mounting thereof on a pMDI dispensing outlet.
Figure 22B:
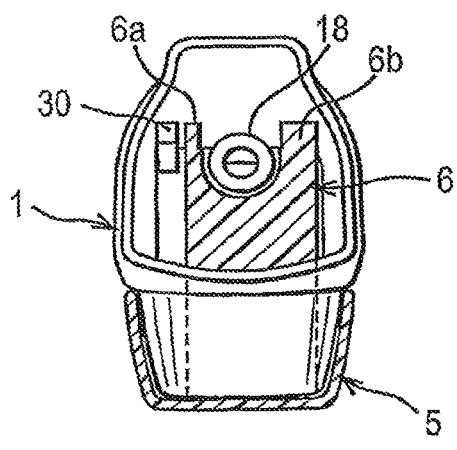
Figure 22C:
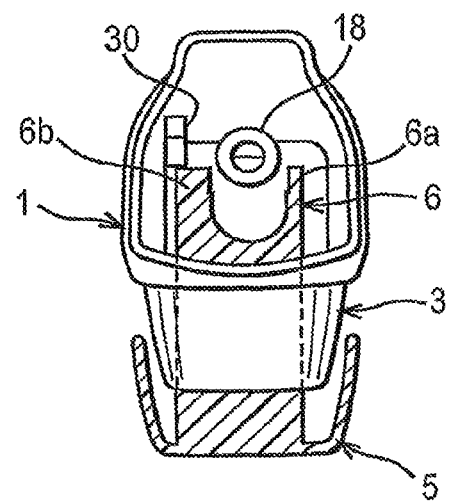

FIG. 22A-22C show a dust cap 5 of a nineteenth embodiment of the invention in which the restricting member 6 is configured and arranged so that it is only insertable through the mouthpiece 3 of the housing 1 to its full extent when the cap 5 is oriented correctly. More particularly, the restricting member is given an asymmetric configuration whereby, in the correct orientation of the cap 5, the arm 6*a* of the restricting member 6 fits between the stem block 18 and the rack 30, and whereby, in the incorrect (inverted) orientation of the cap 5, the arm 6*b* of the restricting member 6 cannot fit between the stem block 18 and the rack 30. Consequently, in the incorrect orientation of the cap 5, the cap 5 is placed outwardly from the mouthpiece 3, as shown in FIG. 22C.

It will be appreciated that the embodiments of the invention described with reference to FIGS. 15 to 22 are to address a possible problem if the dust cap 5 is not mounted to the pMDI housing 1 with the strap 2 or another type of connector. Where the strap 2 or connector is employed, the dust cap 5 will necessarily be presented to the mouthpiece 3 in the correct orientation. Nonetheless, these embodiments may still employ a strap or connector Thus, a wide variety of different embodiments of the invention have been described which all restrict relative movement of the canister unit 14 in the housing the required distance for the dose counter module 14*b* to be actuated and a dose of the medicament formulation to be dispensed. Some of the embodiments also restrict the relative movement such that the canister unit 14 is unable to be removed from the housing 1 until the restricting member is removed or disengaged.

However, it will be appreciated that some embodiments of the invention have utility without inclusion of a restricting member, in particular some of the dust cap embodiments and the 'cap-to-pMDI housing' connector structures. Accordingly, the invention in some of its aspects is not limited to inclusion of a restricting means.

For the avoidance of doubt, it will be appreciated that the present invention is equally applicable where the canister unit 14 does not include the dose counter module 14b. That is to say, the canister unit 14 may simply be the pressurised canister 14a with its valve 50. Alternatively, some other accessory or cap or module may be mounted to the leading end of the canister 14a in place of the dose counter module 14b.

The restricting members of FIGS. 8 to 14 are particularly useful for preventing inadvertent actuation of the pMDI before the pMDI is given to the patient, e.g. through knocks, jolts or jars when being shipped or transported from the manufacturer to the distributor and then to the clinic.

The medicament contained in the canister unit 14 may for the treatment of mild, moderate or severe acute or chronic symptoms or for prophylactic treatment. The medicament is suitably for treating respiratory diseases, e.g. asthma, chronic obstructive pulmonary disease (COPD), although may be for other therapeutic indications, e.g. treating rhinitis.

Appropriate therapeutic agents or medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone (e.g. as the furoate ester), ciclesonide, triamcinolone (e.g. as the acetonide), 6α,9α-difluoro-11β-hydroxy-16α-methyl-3-oxo-17α-propionyloxy-androsta-1,4-diene-17β-carbothioic add S-(2-oxo-tetrahydro-furan-3-yl) ester or 6α,9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)benzo-thiazolone; PDE4 inhibitors e.g. cilomilast or roflumilast; leukotriene antagonists e.g. montelukast, pranlukast and zafirlukast; [adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]; [α4 integrin inhibitors e.g. (2S)-3-[4-{[4-(aminocarbonyl)-1-piperidinyl]carbonyl}oxy)phenyl]-2-[((2S)-4-methyl-2-{[2-(2-ethylphenoxy)acetyl]amino}pentanoyl)amino]propanoic acid (e.g as free acid or potassium salt)], diuretics, e.g., amiloride; anticholinergics, e.g., ipratropium (e.g. as bromide), tiotropium, atropine or oxitropium; hormones, e.g., cortisone, hydrocortisone or prednisolone; xanthines, aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

Preferably, the medicament is formulated in a hydrofluoroalkane propellant, such as HFA-134a or HFA-227 or a combination thereof.

Preferably, the medicament is an anti-inflammatory steroid, such as a corticosteroid, for instance fluticasone, e.g. as the propionate ester, or a long acting beta agonist (LABA), such as salmeterol, e.g. as the xinafoate salt, or a combination thereof.

Preferred medicaments are salmeterol, salbutamol, albuterol, fluticasone and beclomethasone and salts, esters or solvates thereof, for instance fluticasone propionate, albuterol sulphate, salmeterol xinafoate and beclomethasone diproprionate.

The medicament may also be a glucocorticoid compound, which has anti-inflammatory properties. One suitable glucocorticoid compound has the chemical name: 6α,9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α,9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicaments may be delivered in combinations. As an example, there may be provided salbutamol (e.g. as the free base of the sulphate salt) or salmeterol (e.g. as the xinafoate salt) in combination with an anti-inflammatory steroid, such as beclomethasone (e.g. as an ester, preferably dipropionate) or fluticasone (e.g. as an ester, preferably propionate).

It will be understood that the present invention has been described above by way of example only and that the above description should not be taken to impose any limitation on the scope of the claims. Specifically, although the present invention has been described with reference to a pMDI, the invention is not limited to this form of inhaler. The scope of the invention is defined by the appended claims.

The invention claimed is:

1. A pressurized metered dose inhaler (pMDI) comprising a dispensing nozzle and a dust cap for the dispensing nozzle, wherein the dust cap has a cap part adapted for a push-fit on the dispensing nozzle of the pMDI and a strap part for connecting the dust cap to the pMDI, wherein the cap part is slidably mounted on the strap part for sliding movement between an extended position and a contracted position, and wherein the dust cap has a stop mechanism for stopping the cap part in the extended position, and wherein the stop mechanism comprising stop elements on the strap part and the cap part which engage when the cap part is in the extended position, wherein one of the cap part and the strap part comprises a slide member and the other part comprises a track member for the slide member to slide on, and wherein the stop elements are carried by the slide member and the track member, and further wherein a first stop element comprises an opening on one of the slide and track members through which a second stop element on the other part projects, the second stop element having an enlarged section which abuts the edge of the opening in the extended position of the cap part, wherein sliding movement is along an axis and that the opening is oriented transversely to that axis.

2. The pMDI of claim 1, wherein the slide member and the track member define a telescoping arrangement.

3. The pMDI of claim 1, wherein the dust cap has a latching mechanism for latching the cap part in the contracted position.

4. The pMDI of claim 1, wherein the strap part and the cap part have latching elements adapted to latch the cap part in the contracted position.

5. The pMDI of claim 4, wherein the latching elements are carried by the slide and track members.

6. The pMDI of claim 4, wherein the latching elements comprise at least one male latching feature and a corresponding number of complementary female latching features.

7. The pMDI of claim 1, wherein the cap part comprises a cap member for the nozzle.

8. The pMDI of claim 7 wherein the cap member is movably mounted to the slide member or track member.

9. The pMDI of claim 1, wherein the strap part comprises a connector member for connecting the strap part to the pMDI.

10. The pMDI of claim 9 wherein the connector member is movably mounted to the slide member or track member.

11. The pMDI of claim 9, wherein the connector member has an aperture for mounting on a protrusion on the pMDI.

12. The pMDI of claim 11, wherein the aperture has a slot in its boundary surface to increase its flexibility.

13. The pMDI of claim 1, wherein at least one of the cap part and the strap part are integrally formed parts.

14. The pMDI of claim 1, wherein at least one of the cap part and the strap part are of a plastics material.

15. The pMDI of claim 1, wherein the stop mechanism secures the cap and strap parts together.

16. The pMDI of claim 1, wherein one or more projecting elements project into the opening to inhibit extraction of the enlarged section through the opening.

17. The pMDI of claim 1, wherein the dispensing nozzle has a nozzle axis and wherein when the cap part is on the dispensing nozzle the cap part is in its contracted position and the nozzle axis and the axis of sliding movement are oriented in the same direction thereby to enable the cap part to slide to its extended position and be removed from the dispensing nozzle.

* * * * *